US009663444B2

(12) United States Patent
Miller

(10) Patent No.: US 9,663,444 B2
(45) Date of Patent: May 30, 2017

(54) HETEROATOM CONTAINING SUBSTITUTED FATTY ACIDS

(71) Applicant: COMPLEXA, INC., Radnor, PA (US)

(72) Inventor: Raymond A. Miller, Magnolia, OH (US)

(73) Assignee: Complexa, Inc., Radnor, PA (US)

( * ) Notice: Subject to any disclaimer, the term of this patent is extended or adjusted under 35 U.S.C. 154(b) by 0 days.

(21) Appl. No.: 14/205,081

(22) Filed: Mar. 11, 2014

(65) Prior Publication Data

US 2014/0256814 A1 Sep. 11, 2014
US 2017/0113999 A9 Apr. 27, 2017

Related U.S. Application Data

(63) Continuation of application No. 12/896,039, filed on Oct. 1, 2010, now Pat. No. 8,686,167.

(51) Int. Cl.
C07C 205/50 (2006.01)
C07C 317/02 (2006.01)
C07C 69/587 (2006.01)
C07C 57/52 (2006.01)
C07C 211/01 (2006.01)
A61K 31/201 (2006.01)
C07C 323/52 (2006.01)

(52) U.S. Cl.
CPC .......... C07C 205/50 (2013.01); A61K 31/201 (2013.01); C07C 57/52 (2013.01); C07C 69/587 (2013.01); C07C 211/01 (2013.01); C07C 317/02 (2013.01); C07C 323/52 (2013.01)

(58) Field of Classification Search
CPC ... C07C 317/02; C07C 69/587; C07C 205/50; C07C 211/01; C07C 57/52
See application file for complete search history.

(56) References Cited

U.S. PATENT DOCUMENTS

| 3,578,687 | A | 5/1971 | Larkin et al. | |
| 3,819,561 | A | 6/1974 | Bruenner | |
| 3,917,660 | A | 11/1975 | Sasaki et al. | |
| 4,599,430 | A | 7/1986 | Milberger et al. | |
| 5,412,137 | A | 5/1995 | Prashad et al. | 558/146 |
| 5,741,211 | A | 4/1998 | Renirie et al. | |
| 6,187,747 | B1 | 2/2001 | Singh et al. | |
| 6,262,029 | B1 * | 7/2001 | Press et al. | 514/26 |
| 6,346,231 | B1 | 2/2002 | Opheim | |
| 6,376,688 | B1 * | 4/2002 | Ferrante et al. | 554/101 |
| 6,407,075 | B1 | 6/2002 | Scott et al. | |
| 6,410,802 | B1 * | 6/2002 | Dasseux et al. | 568/680 |
| 6,531,150 | B1 | 3/2003 | Sunohara et al. | |
| 6,652,879 | B2 | 11/2003 | Opheim | |
| 6,924,309 | B2 | 8/2005 | Ferrante et al. | |
| 6,998,395 | B2 | 2/2006 | Jackson et al. | |
| 7,312,191 | B2 | 12/2007 | Rose et al. | |
| 7,452,907 | B2 | 11/2008 | Cheng et al. | |
| 7,776,916 | B2 | 8/2010 | Freeman et al. | |
| 7,977,315 | B2 | 7/2011 | Rose et al. | |
| 8,309,526 | B2 | 11/2012 | Freeman et al. | |
| 8,324,277 | B2 | 12/2012 | Freeman | |
| 8,563,609 | B2 | 10/2013 | Miller | |
| 8,686,038 | B2 | 4/2014 | Yang | |
| 8,686,167 | B2 | 4/2014 | Miller | 554/108 |
| 8,735,449 | B2 | 5/2014 | Freeman | |
| 8,933,255 | B2 | 1/2015 | Miller | |
| 8,937,194 | B2 | 1/2015 | Miller | |
| 9,006,473 | B2 | 4/2015 | Freeman et al. | |
| 9,066,902 | B2 | 6/2015 | Freeman et al. | |
| 9,186,408 | B2 | 11/2015 | Freeman et al. | |
| 9,192,600 | B2 | 11/2015 | Yang | |
| 9,271,952 | B2 | 3/2016 | Cushing | |
| 9,295,678 | B2 | 3/2016 | Freeman et al. | |
| 9,308,189 | B2 | 4/2016 | Miller | |
| 2001/0037598 | A1 | 11/2001 | Suppes et al. | |
| 2002/0128510 | A1 | 9/2002 | Durley et al. | |
| 2003/0078299 | A1 | 4/2003 | Ferrante et al. | |
| 2004/0006248 | A1 | 1/2004 | Paiocchi et al. | |
| 2004/0092590 | A1 | 5/2004 | Arterburn et al. | |
| 2004/0147599 | A1 | 7/2004 | Gagnon et al. | |
| 2004/0176451 | A1 | 9/2004 | Tamai et al. | |
| 2004/0254240 | A1 | 12/2004 | Ferrante et al. | |
| 2005/0136103 | A1 | 6/2005 | Ben-Sasson et al. | |
| 2005/0232981 | A1 | 10/2005 | Ben-Sasson | |
| 2006/0018874 | A1 | 1/2006 | Radhakrishnan et al. | |

(Continued)

FOREIGN PATENT DOCUMENTS

EP 1407767 A1 4/2004
EP 1772149 A1 4/2007

(Continued)

OTHER PUBLICATIONS

Napolitano, A. et al., Acid-Promoted reactions of ethyl linoleate with nitrite ions: Formation and structural characterizationof isomeric nitroalkene, hitrohydroxy, and novel 3-nitro-1,5-hexadiene and 1,5-dinitor-1,3-pentadiene products, 2000, Journal of Organic Chemistry, vol. 65, No. 16, pp. 4853-4860.*
Gorczynski, M., et al, Evaluaito of nitroalkenes as nitric oxide donors, 2007, Bioorganic & Medicinal Chemistry Letters, vol. 17, pp. 2013-2017.*
Lima, E.S., et al., Characterizatin of Linoleic Acid Nitration in Human Blood Plasma by Mass Spectrometry, 2002, Biochemistry, vol. 41, No. 34, pp. 10717-10722.*
Manini, P., et al., Chemistry of nitrated lipids: remarkable instability of 9-nitrolinoleic acid in neutral aqueousmediumand a novel nitronitrate ester product by concurrent autoxidation/nitric oxide-release pathways, 2008. J. Org. Chem. vol. 73, No. 19, pp. 7517-7525.*
Woodcock, S. R., et al., Synthesis of nitrolipids. All four possible diasteromers of nitrooleic acids: (E)- and (A), 9- and 10-Nitro-octadec-9-enoic acids, 2006, Organic Letters, vol. 8, No. 18, pp. 3931-3934.*

(Continued)

Primary Examiner — Yate K Cutliff
(74) Attorney, Agent, or Firm — Pepper Hamilton LLP

(57) ABSTRACT

Activated fatty acids, pharmaceutical compositions including activated fatty acids, methods for using activated fatty acids to treat a variety of diseases, and methods for preparing activated fatty acids are provided herein.

11 Claims, No Drawings

(56) References Cited

U.S. PATENT DOCUMENTS

| | | | |
|---|---|---|---|
| 2006/0063953 A1 | 3/2006 | Maurizio et al. | |
| 2006/0100278 A1 | 5/2006 | Cooper et al. | |
| 2006/0241088 A1 | 10/2006 | Arterburn et al. | |
| 2007/0232579 A1* | 10/2007 | Freeman | A61K 31/21 514/178 |
| 2007/0275893 A1 | 11/2007 | Quay | |
| 2008/0096961 A1 | 4/2008 | Serhan et al. | |
| 2009/0326070 A1 | 12/2009 | Freeman et al. | |
| 2010/0166918 A1 | 7/2010 | Miller | |
| 2010/0216884 A1 | 8/2010 | Freeman | |
| 2010/0286257 A1 | 11/2010 | Perricone | |
| 2010/0286271 A1 | 11/2010 | Perricone | |
| 2010/0286272 A1 | 11/2010 | Perricone | |
| 2010/0331268 A1 | 12/2010 | Freeman et al. | |
| 2011/0082206 A1 | 4/2011 | Miller | 514/560 |
| 2011/0092594 A1 | 4/2011 | Yang | |
| 2011/0196037 A1 | 8/2011 | Yang | |
| 2011/0319325 A1 | 12/2011 | Miller | |
| 2012/0136034 A1 | 5/2012 | Freeman et al. | |
| 2013/0059912 A1 | 3/2013 | Freeman | |
| 2013/0101514 A1 | 4/2013 | Cushing | |
| 2013/0210917 A1 | 8/2013 | Freeman et al. | |
| 2014/0024713 A1 | 1/2014 | Yang | |
| 2014/0243380 A1 | 8/2014 | Yang | |
| 2015/0018417 A1 | 1/2015 | Freemen et al. | |
| 2015/0051283 A1 | 2/2015 | Dighiero et al. | |
| 2015/0246059 A1 | 9/2015 | Freeman et al. | |
| 2016/0081961 A1 | 3/2016 | Cushing | |
| 2016/0151318 A1 | 6/2016 | Yang | |
| 2016/0151391 A1 | 6/2016 | Freeman et al. | |

FOREIGN PATENT DOCUMENTS

| | | | |
|---|---|---|---|
| GB | 587992 A | 5/1947 | |
| GB | 1407932 A | 10/1975 | |
| JP | 62132804 | 6/1987 | A01N 37/06 |
| WO | WO 98/09621 A | 3/1998 | |
| WO | WO 01/06983 A2 | 2/2001 | |
| WO | WO 01/15673 A3 | 3/2001 | |
| WO | WO 01/21575 A1 | 3/2001 | |
| WO | WO 01/60778 A2 | 8/2001 | |
| WO | WO 01/78654 A2 | 10/2001 | |
| WO | WO 01/78719 A1 | 10/2001 | |
| WO | WO 01/79156 A1 | 10/2001 | |
| WO | WO 02/22559 A2 | 3/2002 | |
| WO | WO 02/102364 A1 | 12/2002 | |
| WO | WO 03/031399 | 4/2003 | C07C 319/20 |
| WO | WO 03/039533 A1 | 5/2003 | |
| WO | WO 2005/073164 A1 | 8/2005 | |
| WO | WO 2005/110396 | 11/2005 | C07C 229/00 |
| WO | WO 2006/055965 A2 | 5/2006 | |
| WO | WO 2006/086727 A2 | 8/2006 | |
| WO | WO 2007/140433 | 12/2007 | C07K 16/18 |
| WO | WO 2008/008767 A2 | 1/2008 | |
| WO | WO 2008/011085 A1 | 1/2008 | |
| WO | WO 2008/103753 A2 | 8/2008 | |
| WO | WO 2009/017802 A9 | 2/2009 | |
| WO | WO 2009/038671 A2 | 3/2009 | |
| WO | WO 2009/129495 A1 | 10/2009 | |
| WO | WO 2009/134383 A2 | 11/2009 | |
| WO | WO 2009/149496 A1 | 12/2009 | |
| WO | WO 2009/155439 A2 | 12/2009 | |
| WO | WO 2010/042877 A1 | 4/2010 | |
| WO | WO 2010/078504 A1 | 7/2010 | |
| WO | WO 2010/129763 A1 | 11/2010 | |
| WO | WO 2010/129777 A1 | 11/2010 | |
| WO | WO 2011/011882 A1 | 2/2011 | |
| WO | WO 2011/014261 A1 | 2/2011 | |
| WO | WO 2011/098746 A1 | 8/2011 | |

OTHER PUBLICATIONS

Adej, et al., "A Phase I Trial of the Farnesyl Transerase Inhibitor SCH66336: Evidence for Biological and Clinical Activity" *Cancer Research* 60(7): 1871-1877 (2000).

Asakura, N. et al., "Synthesis and biological evaluation of gamma-fluoro-beta, gamma-unstaturated acids" *Journal of Fluorine Chemistry* 127: 800-808 (2006).

Banker, et al., "Modern Pharmaceutics" *Marcel Dekker, Inc., New York* (1979) (TOC).

Baumer, E., "Iodostarin. "Roche" in the treatment of Syphillis" *CAS abstract*, (1 page) (1913).

Blakemore, "The modified Julia olefination: alkene synthesis via the condensation of metallated heteroarylalkysulfones with carbonyl compounds" *J. Chem. Soc., Perkin Trans. 1* 23: 2563-2585 (2002).

Boruwa, et al. "Catalytic Asymmetric Henry Reaction" *Tetrahedron: Asymmetry* 17(24): 3315-3326 (2006).

de Meijere et al., "Metal-Catalyzed Cross-Coupling Reactions" *Wiley-VCH, Weinheim* XXII, ISBN-10: (2004) 3-527-30518-1 and ISBN-13:978-3-527-30518-6 (TOC) (2004).

Dorwald, F.Z., "Side reactions in Organic synthesis" *Wiley-VCH* (20 pages) (2006).

European Search Report from corresponding foreign application, EP 10821313.3, pp. 1-9 (Jul. 2013).

*Goodman & Goldman's the Pharmacological Basis of Therapeuctics, Tenth Edition* (2001), McGraw Hill Book Company, New York, Appendix II, pp. 475-493.

*Goodman & Goldman's the Pharmacological Basis of Therapeutics, Ninth Edition* (1996), McGraw Hill Book Company, New York, Appendix II, pp. 1707-1711, (TOC).

*Goodman & Goldman's the Pharmacological Basis of Therapeutics, Sixth Edition* (1980), MacMillan Publishing Co., New York.

Gorczynski M J et al., "Evaluation of nitroalkenes as nitric oxide donors," *Bioorganic and Medicinal Chemistry Letters, Pergamon, Elsevier Science, GB* 17(7): 2013-2017 Apr. 1, 2007 XP026265844, ISSN: 0960-894X, DOI: 10.1016/J.BMCL.2007.01.016. (Retrieved on Mar. 12, 2007).

Jimenez-Estrada, et al. "Allylic nitration of 3β-sitosterol and cholesterol acetate: Preparation of 7-nitro derivatives" *Steroids* 62(6): 500-503 (1997).

Karp, et al., "Clinical and biological activity of the farnesyltransferase inhibitor R115777 in adults with refractory and relapsed acute leukemias: a phase 1 clinical-laboratory correlative trial" *Blood* 97(11): 3361-3369 (2002).

Kelley, Eric E et al., "Nitro-oleic Acid: A Novel and Irreversible Inhibitor of Xanthine Oxidoreductase," *Journal of Biological Chemistry, American Society for Biochemistry and Molecular Biology US* 283(52): 36176-36184 Dec. 26, 2008, XP002650872, ISSN: 0021-9258, DOI: 10.1074/JBC.M802402200. (Retrieved on Oct. 29, 2009).

Lima, et al. "Cholesteryl nitrolinoleate, a nitrated lipid present in human blood plasma and lipoproteins" *Journal of Lipid Research* 44:1660-1666 (published online Jul. 1, 2003).

Luzzio, "The Henry reaction: recent examples" *Tetrahedron* 57: 915-945 (2001).

March, Advanced Organic Chemistry, McGraw Hill Book Company, New York, (1977 edition) pp. 251-259.

McLean, F., Iodostaring, 1912, Archives of Internal Medicine, vol. 10 (2 pages).

Ono, et al., "A Convenient Procedure for the Conversion of (E)-Nitroalkenes to (Z)-Nitroalkenes via erythro-β-Nitroselenides" *J. Chem. Soc., Chem. Commun.* pp. 1550-1551 (1987).

PCT International Search Report issued in corresponding foreign application, PCT/US2010/051059, pp. 1-4 (2011).

Punchard, N.A., et al., "The Journal of Inflammation, BioMed Central" *The Journal of Inflammation* pp. 1-4 (2004).

Rowe, et al., *Handbook of Pharmaceutical Excipients*, 5th ed., (2006) Great Britain: Pharmaceutical Press; Washington, DC: American Pharmacists Association (TOC).

Scarpini, E. et al., "Treatment of Alzheimer's Disease: Current Status and New Perspectives" *Lancet Neurol*, 2: 539-547 (2003).

(56) References Cited

OTHER PUBLICATIONS

Sharpless, et al., "A Mild Procedure for the Conversion of Epoxides to Allylic Alcohols, the First Organoselenium Reagent" *J. Am. Chem. Soc.* 95(8): 2697-2699 (1973).
Simopoulos, A.P., et al., "Omega-3 Fatty Acids in Inflammation and Autoimmune Diseases" *Journal of the American College of Nutrition* 21(6): 495-505 (2002).
Trostchansky et al., "Nitrated Fatty Acids: Mechanisms of formation, chemical characterization, and biological properties" *Free Radical Biology and Medicine* 44(11): 1887-1896 (published online Mar. 18, 2008).
Woodcock, et al., "Synthesis of Nitrolipids—All Four Diastereomers of Nitrooleic Acids: (E)- and (Z)-, 9-and 10-Nitro-octadec-9-enoic Acids" *Organic Letters* 8(18): 3931-3934 (2006).
Abud-Mendoza et al., "Treating severe systemic lupus erythematosus with rituximab. An open study," *Reumatol. Clin.* 2009, vol. 5, No. 4, 147-152.
Akaike et al., "Antagonistic Action of Imidazolineoxyl N-Oxides against Endothelium-Dreived Relaxing Factor/*no through a Radical Reaction," *Biochem.* 1993, vol. 32, 827-832.
Alber, "Signaling mechanisms of the *Mycobacterium tuberculosis* receptor Ser/Thr protein kinases," *Curr. Opin. Struct. Biol.* Dec. 2009, vol. 19, No. 6, 650-657.
Altschul et al., "Gapped BLAST and PSI-BLAST: a new generation of protein database search programs," *Nucleic Acids Res.* 1997, vol. 25, No. 17, 3389-3402.
Anand et al., "Synthesis and Evaluation of Small Libraries of Triazolylmethoxy Chalcones, Flavanones and 2-aminopyrimidines as Inhibitors of Mycobacterial FAS-II and PknG," *Bioorganic & Medicinal Chem.* 2012, vol. 20, No. 17, 5150-5183.
Arnold et al., "Nitric oxide activates guanylate cyclase and increases guanosine 3':5'-cyclic monophosphate levels in various tissue preparations," *Proc. Natl. Acad. Sci.* 1977. vol. 74, 3203-3207.
Artim et al., "Nitro-oleic acid targets transient receptor potential (TRP) channels in capsaicin sensitive afferent nerves of rat urinary bladder," *Expt. Neurol.* 2011, vol. 232, 90-99.
Baker et al., "Fatty Acid Transduction of Nitric Oxide Signaling," *J. Biol. Chem.* Dec. 23, 2005, vol. 280, No. 51, 42464-42475.
Baker et al., "Convergence of nitric oxide and lipid signaling: Anti-inflammatory nitro-fatty acids," *Free Radic. Biol. Med.* 2009, vol. 46, 989-1003.
Baker et al., "Nitro-fatty Acid Reaction with Glutathione and Cysteine; Kinetic Analysis of Thiol Alkylation by a Michael Addition Reaction," *J. of Biol. Chem.* Oct. 19, 2007, vol. 282, No. 42, 31085-31093.
Baker et al., "Red cell membrane and plasma linoleic acid nitration products: Synthesis, clinical identification, and quantitation," *Proc. Natl. Acad. Sci.* Aug. 10, 2004, vol. 101, No. 32, 11577-11582.
Balazy et al., "Vicinal Nitrohydroxyeicosatrienoic Acids: Vasodilator Lipids Formed by Reaction of Nitrogen Dioxide with Arachidonic Acid," *J. Pharmacol. ExTher.* 2001, vol. 299, No. 2, 611-619.
Balazy, "Isomerization and Nitration of Arachidonic Acid by Nitrogen Dioxide," *Advances in Mass Spectrometry* 2001, vol. 15, 375-376.
Baldus et al., "Endothelial transcytosis of myeloperoxidase confers specificity to vascular ECM proteins as targets of tyrosine nitration," *J. Clin. Invest.* 2001, vol. 108, No. 12, 1759-1770.
Baldus et al., "Is no News Bad News in Acute Respiratory Distress Syndrome," *Am. J. Respir. Crit. Care Med.* 2001, vol. 163, 308-310.
Ballini et al., "Nitroalkanes and Ethyl Glyoxalate as Common Precursors for the Preparation of both β-keto Esters and α,β-unsaturated Esters," *Tetrahedron Letters* 2004, vol. 45, 7027-7029.
Ballini et al., "Fast Diastereoselective Baylis-Hillman Reaction by Nitroalkenes: Synthesis of Di- and Triene Derivatives," *Tetrahedron* 2004, vol. 60, 4995-4999.
Ballini et al., "(Z)-7-Nitro-3-Heptene as Central Intermediate for the Synthesis of Jasmone, Methyl Jasmonate and γ-Jasmolactone," *Synthetic Communications* 1989, vol. 19, Nos. 3-4, 575-583.

Bates et al., "Nitroalkene Fatty Acids Mediate Activation of Nrf2/ARE-Dependent and PPARγ-Dependent Transcription by Distinct Signaling Pathways and with Significantly Different Potencies," *Biochem.* 2011, vol. 50, 7765-7773.
Bates et al., "Noncatalytic Interactions between Glutathione S-Transferases and Nitroalkene Fatty Acids Modulate Nitroalkene-Mediated Activation of Peroxisomal Proliferator-Activated Receptor γ," *Biochem.* 2009, vol. 48, 4159-4169.
Batthyany et al., "Reversible Post-translational Modification of Proteins by Nitrated Fatty Acids In Vivo," *J. Biol. Chem.* Jul. 21, 2006, vol. 281, No. 29, 20450-20463.
Beckman et al., "Apparent hydroxyl radical production by peroxynitrite. Implications for endothelial injury from nitric oxide and superoxide," *Proc. Natl. Acad. Sci.* 1990, vol. 87, 1620-1624.
Bell-Parikh et al., "Biosynthesis of 15-deoxy-$\Delta^{12,14}$-PGJ$_2$ and the ligation of PPARγ," *J. Clin. Invest.* 2003, vol. 112, No. 6, 945-955.
Bennett et al., *Cecil Textbook of Medicine* 1996, 20$^{th}$ Ed., vol. 1, 1004-1010.
Biegert et al., "Sequence Context-specific Profiles for Homology Searching," *PNAS* 2009, vol. 106, No. 10, 3770-3775.
Bjorn, "Clues emerge about benefits of briefly blocking blood flow," *Nature* Feb. 2009, vol. 15, No. 2, 132.
Blair et al., "Bathophenanthrolinedisulphonic Acid and Bathocuproinedisulphonic Acid, Water Soluble Reagents for Iron and Copper," *Talanta* 1961, vol. 7, Nos. 3-4, 163-174 (abstract).
Blanco et al., "6-Methylnitroarachidonate: A novel esterified nitroalkene that potently inhibits platelet aggregation and exerts cGMP-mediated vascular relaxation," *Free Radic. Biol. Med.* 2011, vol. 50, 411-418.
Bligh et al., "A Rapid Method of Total Lipid Extraction and Purification," *Can. J. Biochem. Physiol.* 1959, vol. 37, No. 8, 911-917.
Bloodsworth et al., "Nitric Oxide Regulation of Free Radical- and Enzyme-Medicated Lipid and Lipoprotein Oxidation," *Arterioscler. Thromb. Vasc. Biol.* Jul. 2000, vol. 20, 1707-1715.
Boden et al., "Free fatty acids in obesity and type 2 diabetes: defining their role in the development of insulin resistance and β-cell dysfunction," *Euro. J. Clin. Invest.* 2002, 32 (Suppl. 3), 14-23.
Bonacci et al., "Gas-Phase Fragmentation Analysis of Nitro-Fatty Acids," *J. Am. Soc. Mass Spec.* 2011, vol. 22, 1534-1551.
Bonacci et al., "Nitro-oleic Acid Improves Insulin Signaling via Protein Tyrosine Phosphatase-1b Inhibition," *Free Radical Bio. Med.* Jan. 1, 2008, Elsevier Science, vol. 45, Suppl. 1, S154 (abstract).
Bonacci et al., "Electrophilic Fatty Acids Regulate Matrix Metalloproteinase Activity and Expression," *J. Biolo. Chem.* 2011, vol. 286, No. 18, 16074-16081 (abstract).
Bonomi et al., "Direct Metal Ion Substitution at the [M(Scys)$_4$]$^2$ Site of Rubredoxin," *J. Biol. Inorg. Chem.* 1998, vol. 3, No. 6, 595-605.
Borniquel et al., "Nitrated oleic acid up-regulates PPARγ and attenuates experimental inflammatory bowel disease," *Free Radic. Bio. Med.* 2010, vol. 49, Iss. 4, 499-505.
Burdge, "α-Linolenic Acid Metabolism in Men and Women: Nutritional and Biological Implications," *Clin. Nutri. Metabol. Care* 2004, vol. 7, 137-144.
Canadian Office Action issued on Apr. 24, 2015, by the Canadian Patent Office in corresponding Canadian Patent Application No. 2,729,053.
Cannon, *Burger's Medicinal Chemistry and Drug Discovery* 1995, Fifth Edition, vol. I: Principles and Practice, Chap. 19, John Wiley & Sons, Inc., 783-802.
Castro et al., "Cytochrome c: a catalyst and target of nitrate-hydrogen peroxide-dependent protein nitration," *Arch. Biochem. Biophys.* 2004, vol. 421, 99-107.
Chawla et al., "PPAR-γ dependent and independent effects on macrophage-gene expression in lipid metabolism and inflammation," *Nat. Med.* 2001, vol. 7, No. 1, 48-52.
Chen et al., "Peroxisome Proliferator-Activated Receptors and the Cardiovascular System," *Vitam. Horm.* 2003, vol. 66, 157-188.
Chen et al., "Synthesis and Screening of Novel Vitamin E Derivatives for Anticancer Functions," *European J. of Medicinal Chem.* 2012, vol. 58, 72-83.

(56) References Cited

OTHER PUBLICATIONS

Chen et al., "Troglitazone Inhibits Aterhosclerosis in Apolipoprotein E-Knockout Mice: Pleiotropic Effects on CD36 Expression and HDL," *Arterioscler. Thromb. Vasc. Biol.* 2001, vol. 21, 372-377.
Chinese First Office Action issued on Feb. 25, 2013, in Chinese Application No. 200980125943.4.
Clapp et al., "Oxygenation of Monounsaturated Fatty Acids by Soybean Liposygenase-1: Evidence for Transient Hydroperoxide Formation," *Biochem.* 2006, vol. 45, 15884-15892.
Claudel et al., "Reduction of atherosclerosis in apolipoprotein E knockout mice by activation of the retinoid X receptor," *Proc. Natl. Acad. Sci.* 2001, vol. 98, No. 5, 2610-2615.
Coffey et al., "Catalytic consumption of nitric oxide by 12/15-lipoxygenase. Inhibition of monocyte soluble guanylate cyclase activation," *Proc. Natl. Acad. Sci.* Jul. 3, 2001, vol. 98, No. 14, 8006-8011.
Cole et al., "Deciphering the Biology of *Mycobacterium tuberculosis* from the Complete Genome Sequence," *Nature* 1998, vol. 393, 537-544.
Cole et al., "Nitro-Fatty Acid Inhibition of Neointima Formation After Endoluminal Vessel Injury," *Circ. Res.* Nov. 6, 2009, 1-8; Suppl. Materials 1-6.
Coles et al., "Nitrolinoleate Inhibits Platelet Activation by Attenuating Calcium Mobilization and Inducing Phosphorylation of Vasodilator-stimulated Phosphoprotein through Elevation of cAMP," *J. Biol. Chem.* Feb. 22, 2002, vol. 277, No. 8, 5832-5840.
Coles et al., "Nitrolinoleate Inhibits Superoxide Generation, Degranulation, and Integrin Expression by Human Neutrophils. Novel Antiinflammatory Properties of Nitric Oxide-Derived Reactive Species in Vascular Cells," *Circ. Res.* Sep. 6, 2002, vol. 91, 375-381.
Collins et al., "Troglitazone Inhibits Formation of Early Atherosclerotic Lesions in Diabetic and Nondiabetic Low Density Lipoprotein Receptor-Deficient Mice," *Arterioscler. Thromb. Vasc. Biol.* 2001, vol. 21, 365-371.
Communication pursuant to Article 94(3) EPC for European Application No. 08 780 348.2 dated Jul. 26, 2011.
Cosby et al., "Nitrite reduction to nitric oxide by deoxyhemoglobin vasodilates the human circulation," *Nat. Med.* 2003, vol. 9, No. 12, 1498-1505.
Cowley et al., "The *Mycobacterium tuberculosis* Protein Serine/threonine Kinase PknG Is Linked to Cellular Glutamate/glutamine Levels and Is Important for Growth In Vivo," *Molecular Microbio.* 2004, vol. 52, No. 6, 1691-1702.
Cui et al., "Nitrated Fatty Acids: Endogenous Anti-inflammatory Signaling Mediators," *J. Biol. Chem.* Nov. 24, 2006, vol. 281, No. 47, 35686-35698.
Dang et al. (Hung), "Anti-inflammatory Constituents of the Red Alga *Gracilaria verrucosa* and Their Synthetic Analogues," *J. Nat. Prod.* 2008, vol. 71, No. 2, 232-240.
Dangi et al., "Biogenic Synthesis, Purification, and Chemical Characterization of Anti-Inflammatory Resolvins Derived from Docosapentaenoic Acid (DPAn-6)," *J. Biol. Chem.* May 29, 2009, vol. 284, No. 22, 14744-14759.
Davies et al., "Oxidized Alkyl Phospholipids Are Specific, High Affinity Peroxisome Proliferator-activated Receptor γ Ligands and Agonists," *J. Biol. Chem.* May 11, 2001, vol. 276, No. 19, 16015-16023.
Defronzo et al., "Insulin Resistance: A Multifaceted Syndrome Responsible for NIDDM, Obesity, Hypertension, Dyslipidemia, and Atherosclerotic Cardiovascular Disease," *Diabetes Care* Mar. 1991, vol. 14, No. 3, 175-194.
Delerive et al., "Oxidized Phospholipids Activated PPARα in a Phospholipase A2-Dependent Manner," *FEBS Lett.* 2000, vol. 471, 34-38.
Del Mar Gras Sa et al., "Daily Oral Oleoyl-estrone Gavage Induces a Dose-dependent Loss of Fat in Wistar Rats," *Obesity Res.* Mar. 1, 2001, vol. 9, No. 3, 202-209.

Denicola et al., "Diffusion of Nitric Oxide into Low Density Lipoprotein," *J. Biol. Chem.* 2002, vol. 277, No. 2, 932-936.
Denicola et al., "Diffusion of peroxynitrite across erythrocyte membranes," *Proc. Natl. Acad. Sci.* 1998, vol. 95, 3566-3571.
Desper et al., "Getting a Tree Fast: Neighbor Joining, FastME, and Distance-Based Methods," *Curr. Protoc. Bioinformatics* 2006, Chap. 6, Unit 6.3.
Diabetic ketoacidosis in www.mayoclinic.org/diseases-conditions/diabetic-ketoacidosis/basics/treatment/con-20026470 (retrieved from the internet Jan. 21, 2016).
d'Ischia, "Oxygen-Dependent Nitration of Ethyl Linoleate with Nitric Oxide," *Tetrahedron Lett.* 1996, vol. 37, No. 32, 5773-5774.
d'Ischia et al., "Medium-dependent Competitive Pathways in the Reactions of Polyunsaturated Fatty Acids with Nitric Oxide in the Presence of Oxygen. Structural Characterisation of Nitration Products and a Theoretical Insight," *Tetrahedron* 1999, vol. 55, 9297-9308.
Dodge et al., "Composition of phospholipids and of phospholipids fatty acids and aldehydes in human red cells," *J. Lipid Res.* 1967, vol. 8, 667-675.
Doksorubitsin-Ebeve, Instruksiya po primeneniyu lekarstvennogo perparata dlya meditinskogo primeneniya, Retrieved from the Internet: Nov. 19, 2014, http://medi.ru/doc/f4509.htm. No translation available.
Easton et al., "Polyunsaturated Nitroalkanes and Nitro-Substituted Fatty Acides," *Synthesis* 2001, vol. 3, 451-457.
Eberhardt et al., "Prevalence of Overweight and Obesity Among Adults with Diagnosed Diabetes—United States, 1988-1994 and 1999-2002," *CDC*, Nov. 19, 2004; vol. 53, No. 45, 1066-1068.
Eiserich et al., "Myeloperoxidase, a Leukocyte-Derived Vascular NO Oxidase," *Sci.* Jun. 28, 2002, vol. 296, 2391-2394.
Eiserich et al., "Pathophysiology of Nitric Oxide and Related Species: Free Radical Reactions and Modification of Biomolecules," *Molec. Aspects Med.* 1998, vol. 19, 221-357.
EP Communication issued on European Patent Application No. 09767748.8 dated Dec. 27, 2011.
Escudier et al., "Bevacizumab plus interferon alfa-2a for treatment of metastatic renal cell carcinoma: a randomized, double-blind phase III trial," *The Lancet* Dec. 22-29, 2007, vol. 370, 2103-2111.
European Examination Report issued in corresponding foreign application, EP Appl. 09767748.8, 1-3, dated Oct. 23, 2012.
European Office Action issued on Jul. 9, 2013, by the European Patent Office, in corresponding European Patent Application No. 09739186.6.
European Office Action issued on Dec. 19, 2014, by the European Patent Office, in corresponding European Patent Application No. 09739186.6.
Evans et al., "PPARs and the complex journey to obesity," *Nat. Med.* Apr. 2004, vol. 10, No. 4, 1-7.
Extended European Search Report and Written Opinion issued in corresponding foreign application, EP 11804082.3, 1-5 (Nov. 29, 2013).
Extended European Search Report and Written Opinion issued in corresponding European Patent Application No. 12825790.4, 1-7 (Dec. 11, 2014).
Extended European Search Report and Written Opinion issued in corresponding European Patent Application No. 12839555.5, 1-6 (Feb. 2, 2015).
Extended European Search Report and Written Opinion issued in corresponding European Patent Application No. 09767748.8, 1-6 (Dec. 8, 2011).
Extended European Search Report for EP08780348.2 (Jul. 30, 2010).
Extended European Search Report and Written Opinion issued in EP Patent Application No. 09732031.1 dated Dec. 22, 2011.
Extended European Search Report and Written Opinion issued in EP Patent Application No. 13743207.6-1464, dated Jun. 22, 2015.
Feelisch et al., "Concomitant S-, N-, and heme-nitros(yl)ation in biological tissues and fluids: implications for the fate of NO in vivo," *FASEB J.* Nov. 2002, vol. 16, 1775-1785.
Ferreira et al., "Macrophage activation induces formation of the anti-inflammatory lipid cholesteryl-nitrolinoleate," *Biochem. J.* 2009, vol. 417, 223-234.

(56) References Cited

OTHER PUBLICATIONS

Ferry et al., "Binding of prostaglandins to human PPARγ: tool assessment and new natural ligands," *Eur. J. Pharmacol.* 2001, vol. 417, 77-89.
Final Office Action dated Jul. 7, 2014, issued for U.S. Appl. No. 13/387,489.
Finlayson-Pitts et al., "A Fourier Transform Infrared Spectrometry Study of the Reactions of Phosphatidylcholines with Gaseous $N_2O_5$ and $NO_2$," *Toxicol. Appl. Pharmacol.* 1987, vol. 89, 438-448.
Fiuza et al., "From the Characterization of the Four Serine/Threonine Protein Kinases (PknA/B/G/L) of Corynebacterium Glutamicum Toward the Role of PknA and PknB in Cell Division," *J. Biolo. Chem.* 2008, vol. 283, No. 26, 10899-18112.
Forman et al., "15-Deoxy-$\Delta^{12,14}$-Prostaglandin $J_2$ is a Ligand for the Adipocyte Determination Factory PPARγ," *Cell* 1995, vol. 83, 803-812.
Freeman et al., "Nitro-fatty Acid Formation and Signaling," *J. of Biol. Chem.* Jun. 6, 2008, vol. 283, No. 23, 15515-15519.
Freshney, "Culture of Animal Cells," *A Manual of Basic Technique* 1983, Alan R. Liss, Inc., New York, 1-6.
Fu et al., "Oleylethanolamide regulates feeding and body weight through activation of the nuclear receptor PPAR-α," *Nature* Sep. 4, 2003, vol. 425, 90-93.
Furstner et al., "Total Synthesis of Epohelmin B and Its Analogues," *Chem. Asian J.* 2008, vol. 3, 310-318.
Gallon et al., "The Identification of the Allylic Nitrite and Nitro Derivatives of Methyl Linoleate and Methyl Linolenate by Negative Chemical Ionization Mass Spectroscopy," *Lipids* 1993, vol. 28, No. 2, 125-133.
Gallon et al., "The Reaction of Low Levels of Nitrogen Dioxide with Methyl Linoleate in the Presence and Absence of Oxygen," *Lipids* 1994, vol. 29, No. 3, 171-176.
Gavin III et al., "Reducing Cardiovascular Disease Risk in Patients with Type 2 Diabetes: A Message from the National Diabetes Education Program," *Am. Fam. Physician* Oct. 15, 2003, vol. 68, No. 8, 1569-74.
Gladwin et al., "The emerging biology of the nitrite anion," *Nature* Nov. 2005, vol. 1, No. 6, 308-314.
Gladwin et al., "Role of circulating nitrite and S-nitrosohemoglobin in the regulation of regional blood flow in humans," *Proc. Natl. Acad. Sci.* 2000, vol. 97, No. 21, 11482-11487.
Gladwin et al., "S-Nitrosohemoglobin Is Unstable in the Reductive Erythrocyte Environment and Lacks $O_2$/NO-linked Allosteric Function," *J. Biol. Chem.* 2002, vol. 277, No. 31, 27818-27828.
Glauser et al., "The inflammatory response and tissue damage. The example of renal scars following acute renal infection," *Pediatric Nephrology* Oct. 1987, vol. 1, No. 4, 615-622 (Abstract) (from PubMed website Jan. 22, 2016).
Gorczynski et al., "Regio-and Stereospecific Synthesis and Nitric Oxide Donor Properties of (E)-9- and (E)-10-Nitrooctadec-9-enoic Acids," *Org. Lett.* Apr. 25, 2006, vol. 8, No. 11, 2305-2308.
Gregory et al., "5-$HT_3$ Receptor Antogonists for the Prevention of Chemotherapy-Induced Nausea and Vomiting: A Comparison of Their Pharmacoogy and Clinical Efficacy," *Drugs* Feb. 1998, vol. 55, No. 2, 173-189.
Grisham, "Myoglobin-Catalyzed Hydrogen Peroxide Dependent Arachidonic Acid Peroxidation," *Free Radic. Biol. Med.* 1985, vol. 1, 227-232.
Groeger et al., "Discovery, Structural Characterization and Quantification of Novel Inflammatory-Induced Electrophilic Fatty Acid Derivatives," *Free Radical Biology & Medicine* 2008, vol. 45, No. 1, S134.
Groeger et al., "Cyclooxygenase-2 generates anti-inflammatory mediators from omega-3 fatty acids," *Nat. Chem. Bio.* Jun. 2010, vol. 6, 433-441.
Groeger et al., "Signaling Actions of Electrophiles: Anti-inflammatory Therapeutic Candidates," *Molec. Interven.* Feb. 2010, vol. 10, Issue 1, 39-50.
Guindon et al., "A Simple, Fast, and Accurate Algorithm to Estimate Large Phylogenies by Maximum Likelihood," *Systematic Bio.* 2003, vol. 52, No. 5, 696-704.
Guindon et al., "Estimating Maximum Likelihood Phylogenies with PhyML," *Methods in Molecular Bio.* 2009, vol. 537, 113-137.
Guo et al., "Atypical PKCζ transduces electrophilic fatty acid signaling in pulmonary epithelial cells," *Nitric Oxide* 2011, vol. 25, 366-372.
Gutierrez et al., "Nitric Oxide Regulation of Superoxide-Dependent Lung Injury: Oxidant-Protective Actions of Endogenously Produced and Exogenously Administered Nitric Oxide," *Free Radic. Biol. Med.* 1996, vol. 21, No. 1, 43-52.
Hartmann et al., "A randomized trial comparing the nephrotoxicity of cisplatin/ifosfamide-based combination chemotherapy with or without amifostine in patients with solid tumors," *Investigational New Drugs* 2000, vol. 18, 281-289.
Hogg et al., "Reactions of Nitric Oxide With Nitronyl Nitroxides and Oxygen: Prediction of Nitrate Formation By Kinetic Simulation," *Free Radic. Res.* 1995, vol. 22, No. 1, 47-56.
Hogg et al., "Inhibition of low-density lipoprotein oxidation by nitric oxide Potential role in atherogenesis," *FEBS Lett.* 1993, vol. 334, No. 2, 170-174.
Hogg, "The Biochemistry and Physiology of S-nitrosothiols," *Annu. Rev. Pharmacol. Toxicol.* 2002, 42, 585-600.
Ichikawa et al., "Nitroalkenes Suppress Lipopolysaccharide-Induced Signal Transducer and Activator of Transcription Signaling in Macrophages: A Critical Role of Mitogen-Activated Protein Kinase Phosphatase 1," *Endocrinology* May 8, 2008, vol. 149, No. 8, 4086-4094.
Ignarro et al., "Endothelium-Derived Relaxing Factor From Pulmonary Artery and Vein Possesses Pharmacologic and Chemical Properties Identical to Those of Nitric Oxide Radical," *Circ. Res.* 1987, vol. 61, 866-879.
Ignarro et al., "Pharmacological Evidence that Endothelium-Derived Relaxing Factor is Nitric Oxide: Use of Pyrogallol and Superoxide Dismutase to Study Endothelium-Dependent and Nitric Oxide-Elicted Vascular Smooth Muscle Relaxation," *J. Pharmacol. ExTher.* 1988, vol. 244, No. 1, 181-189.
Iles et al., "Fatty acid transduction of nitric oxide signaling: nitrolinoleic acid mediates protective effects through regulation of the ERK pathway," *Free Radic. Biol. Med.* 2009, vol. 46, 866-875.
International Preliminary Report on Patentability issued in corresponding PCT/US2009/0047825, Jan. 6, 2011.
International Preliminary Report on Patentability issued in corresponding PCT/US2012/051304, 1-8 (Mar. 6, 2014).
International Preliminary Report on Patentability issued in corresponding PCT/US2012/059722, 1-9 (Apr. 24, 2014).
International Search Report and Written Opinion mailed Dec. 4, 2009 corresponding to PCT/US2009/002628.
International Search Report and Written Opinion mailed Apr. 21, 2015 corresponding to PCT/US2014/065203.
International Search Report and Written Opinion mailed Aug. 19, 2013 corresponding to PCT/US2012/059722.
International Search Report and Written Opinion mailed Jun. 2, 2013 corresponding to PCT/US2013/024476.
International Search Report and Written Opinion mailed Jun. 30, 2009 corresponding to PCT/US2009/041018.
International Search Report and Written Opinion mailed Mar. 23, 2012 corresponding to PCT/US2011/042011.
International Search Report and Written Opinion mailed Mar. 5, 2010 corresponding to PCT/US2009/047825.
International Search Report and Written Opinion mailed Nov. 1, 2012 corresponding to PCT/US2012/051304.
International Search Report and Written Opinion mailed Nov. 27, 2014 corresponding to PCT/US2014/047073.
International Search Report and Written Opinion mailed Oct. 12, 2006 corresponding to International Patent Application No. PCT/US2005/014305.
International Search Report and Written Opinion mailed Oct. 24, 2008 corresponding to International Patent Application No. PCT/US2008/009274.
International Search Report PCT/US2010/002141 dated Nov. 24, 2010.

(56) References Cited

OTHER PUBLICATIONS

Itoh et al., "Synthesis of Docosahexaenoic Acid Derivatives Designed as Novel PPARγ Agonists and Antidiabetic Agents," *Bioorg. Med. Chem.* 2006, vol. 14, 98-108.
Janero et al., "Differential nitros(yl)ation of blood and tissue constituents during glyceral trinitrate biotransformation in vivo," *PNAS* Nov. 30, 2004, vol. 101, No. 48, 16958-16963.
Japanese Office Action issued May 12, 2014, in Japanese Patent Application No. 2011-507440.
Japanese Office Action issued Oct. 15, 2013, in Japanese Patent Application No. 2011-507440.
Jeong et al., "Fenofibrate Prevents Obesity and Hypertriglyceridemia in Low-Density Lipoprotein Receptor-Null Mice," *Metabolism* May 2004, vol. 53, No. 5, 607-613.
Jourd'Heuil et al., "The Oxidative and Nitrosative Chemistry of the Nitric Oxide/Superoxide Reaction in the Presence of Bicarbonate," *Arch. Biochem. Biophys.* 1999, vol. 365, No. 1, 92-100.
Junping et al., "Pharmacokinetics and antitumor effects of vincristine carried microemulsions composed of PEG-lipid, oleic acid, vitamin E and cholesterol," *Int. J. Pharm.* Jan. 30, 2003, vol. 251, No. 1-2, 13-21, abstract provided.
Kansanen et al., "Nrf2-Dependent and -Independent Responses to Nitro-fatty Acids in Human Endothelial Cells: Identification of Heat Shock Response as the Major Pathway Activated by Nitro- oleic Acid," *J. Biol. Chem.* Oct. 5, 2009, 1-34.
Katoh et al., "Recent Developments in the MAFFT Multiple Sequence Alignment Program," *Briefings in Bioinformatics* 2008, vol. 9, No. 4, 286-298.
Khoo et al., "Activation of vascular endothelial nitric oxide synthase and heme oxygenase-1 expression by electrophilic nitro-fatty acids," *Free Radic. Bio. Med.* 2010, vol. 48, 230-239.
Khoo et al., "Electrophilic nitro-fatty acids: anti-inflammatory mediators in the vascular compartment," *Curr. Opn. Pharml.* 2010, vol. 10, 179-184.
Kim et al., "Bisubstrate Ketone Analogues as Serotonin N-Acetyltransferase Inhibitors," *J. Med. Chem.* 2001, vol. 44, No. 15, 2479-2485.
Kissner et al., "Formation and Properties of Peroxynitrite as Studied by Laser Flash Photolysis, High-Pressure Stopped-Flow Technique, and Pulse Radiolysis," *Chem. Res. Toxicol.* Sep. 4, 1997, vol. 10, 1285-1292.
Kliewer et al. "A Prostaglandin $J_2$ Metabolite Binds Peroxisome Proliferatory-Activated Receptor γ and Promotes Adipocyte Differentiation," *Cell* 1995, vol. 83, 813-819.
Kliewer et al., "Fatty acids and eicosanoids regulate gene expression through direct interactions and peroxisome proliferator-activated receptors α and γ," *Proc. Natl. Acad. Sci.* Apr. 1997, vol. 94, 4318-4323.
Kobayshi, "The Reaction of Nitrogen Dioxide with Lung Surface Components: The Reaction with cis-9-octadecenoic Acid," *Chemosphere* 1983, vol. 12, No. 9/10, 1317-1325.
Koenitzer et al., "Redox signaling in inflammation: interactions of endogenous ,lectrophiles and mitochondria in cardiovascular disease," *Ann. N.Y. Acad. Sci.* 2010, vol. 1203, 45-52.
Kunin, "Urinary Tract Infections in Females," *Clinical Infectious Diseases*, Jan. 1994, vol. 18, 1-10.
Lai et al., "Reactions of Dinitrogen Pentoxide and Nitrogen Dioxide with 1-Palmitoyl-2-Oleoyl-sn-Glycero-3-Phosphocholine," *Lipids* 1991, vol. 26(4), 306-314. Abstract.
Lärfars et al., "Activation of Nitric Oxide Release and Oxidative Metabolism by Leukotrienes B4, C4, and D4 in Human Polymorphonuclear Leukocytes," *Blood* Feb. 15, 1999, vol. 93, No. 4, 1399-1405.
Lee et al., "Peroxisome proliferators-activated receptor-γ in macrophage lipid homeostasis," *Trends Endocrinol. Metab.* Oct. 2002, vol. 13, No. 8, 331-335.
Lee et al., "Rosiglitazone ameliorates cisplatin-induced renal injury in mice," *Nephrol. Dial. Transplant.* May 23, 2006, vol. 21, 2096-2105.
Levy et al., "Lipid mediator class switching during acute inflammation: signals in resolution," *Nat. Immunol.* Jul. 2001, vol. 2, No. 7, 612-619.
Li et al., "Molecular recognition of nitrated fatty acids by PPARγ," *Nat. Struct. Mol. Biol.* 2008, 1-3.
Li et al., "Differential inhibition of macrophage foam-cell formation and atherosclerosis in mice by PPARalpha, betta/delta, and gamma," *J. Clin. Invest.* 2004, vol. 114, No. 11, 1564-1576.
Li et al., "PPARα Ligand Protects During Cisplatin-Induced Acute Renal Failure by Preventing Inhibition of Renal FAO and PDC Activity," *Am. J. Physiol. Renal Physiol.* Nov. 11, 2003, vol. 286, F572-F580.
Lim et al., "Nitrolinoleate, a nitric oxide-derived mediator of cell function: Synthesis, characterization, and vasomotor activity," *Proc. Natl. Acad. Sci.* Dec. 10, 2002, vol. 99, No. 25, 15941-15946.
Lima et al., "Characterization of Linoleic Acid Nitration in Human Blood Plasma by Mass Spectrometry," *Biochem.* 2002, vol. 41, No. 34, 10717-10722.
Lima et al., "Nitrated Lipids Decompose to Nitric Oxide and Lipid Radicals and Cause Vasorelaxation," *Free Radical Bio. Med.* 2005, Elsevier Sciences, vol. 39, No. 4, 532-539.
Liu et al., "Accelerated reaction of nitric oxide with $O_2$ within the hydrophobic interior of biological membranes," *Proc. Natl. Acad. Sci.* Mar. 1998, vol. 95, 2175-2179.
Liu et al., "Combined losartan and nitro-oleic acid remarkably improves diabetic nephrophaty in mice," *Am. J. Physiol. Renal Physiol.* Aug. 14, 2013, vol. 305, F1555-F1562.
Liu et al., "Nitrol-Oleic Acid Protects the Mouse Kidney from Ischemia and Reperfusion Injury," *Am. J. Physiol. Renal Physiol.* Aug. 27, 2008, vol. 295, F942-F949.
Lopez et al., "Second Generation of α-Tocopherol Analogs-Nitric Oxide Donors: Synthesis, Physiochemical, and Biological Characterization," *Bioorg. Med. Chem.* 2007, vol. 15, 6262-6272.
Löytynoja et al., "An Algorithm for Progressive Multiple Alignment of Sequences with Insertions," *PNAS* Jul. 26, 2005, vol. 102, No. 30, 10557-10562.
Lundberg et al., "Nitrate and nitrite in biology, nutrition and therapeutics," *Nat. Chem. Bio.* Dec. 2009, vol. 5, No. 12, 865-869.
Ma et al., "Hydrohalogenation Reaction of Substituted 1, 2-Allenic Carboxylic Acids, Esters, Amides, Nitriles, and Diphenyl Phosphine Oxides," *Synthesis* Dec. 4, 2001, No. 5, 713-730.
Marnett et al., "Regulation of Prostaglandin Biosynthesis by Nitric Oxide Is Revealed by Targeted Deletion of Inducible Nitric-oxide Synthese," *J. Biol. Chem.* 2000, vol. 275, No. 18, 13427-13430.
Marshall et al., "Nitrosation and oxidation in the regulation of gene expression," *FASEB J.* 2000, vol. 14, 1889-1900.
Marx et al., "Peroxisome Proliferator-Activated Receptors and Atherogenesis: Regulators of Gene Expression in Vascular Cells," *Circ. Res.* May 14, 2004, vol. 94, No. 9, 1168-1178.
McIntyre et al., "Identification of an intracellular receptor for lysophosphatidic acid (LPA): LPA is a transcellular PPARγ agonist," *Proc. Natl. Acad. Sci.* 2003, vol. 100(1), 131-136.
Menendez et al., "Effects of gama-linolenic acid and oleic acid on paclitaxel cytotoxicity in human breast cancer cells," *European J. of Cancer* (Oxford, England: 1990) Feb. 2001, vol. 37, No. 3, 402-213.
Messerschmidt et al., *Handbook of Metalloproteins* 2001, Hoboken, NJ, John Wiley & Sons, Inc. (abstract).
Metabolite definition athttps://www.nlm.nih.gov/medlineplus/ency/article/002258.htm (retrieved from the internet Jan. 21, 2016).
Meyer et al., "Uremia," *New Engl. J. Med.* Sep. 27, 2007, vol. 357, 1316-1325.
Minghetti, "Cyclooxygenase-2 (COX-2) in Inflammatory and Degenerative Brain Diseases," *J. Neuropathol. Exp. Neurol.* Sep. 2004, vol. 63, No. 9, 901-910.
Miranda et al., "The Chemical Biology of Nitric Oxide," *Nitric Oxide: Biology and Pathobiology* 2000, Academic Press, San Diego, 41-55.
Mitschke et al., "9- and 10-Nitro-oleic Acid Do Not Interfere with the GC-MS Quantitative Determination of Nitrite and Nitrate in Biological Fluids When Measured as Their Pentalfluorobenzyl Derivatives," *J. Chromatography B.* 2007, vol. 85, Issue 1, 287-291.
Montuschi et al., "Isoprostanes: markers and mediators of oxidative stress," *FASEB J.* Dec. 2004, vol. 18, 1791-1800.

(56) References Cited

OTHER PUBLICATIONS

Morgan et al., "Use of Animal Models of Human Disease for Nonclinical Safety Assessment of Novel Pharmaceuticals," *Toxicol. Pathol.* 2013, vol. 41, No. 3, 508-518.

Mukherjee et al., "A Selective Peroxisome Proliferator-Activated Receptor-γ (PPARγ) Modulatory Blocks Adipocyte Differentiation byt Stimulates Glucose uptake in 3T3-L1 Adipocytes," *Mol. Endocrinol.* 2000, vol. 14, 1425-1433.

Nadtochiy et al. "Mitochondrial nitroalkene formation and mild uncoupling in ischaemic preconditioning: implications for cardioprotection," *Card. Res. Adv. Access* 2008, 1-8.

Nadtochiy et al., "Nitroalkenes Confer Acute Cardioprotection via Adenine Nucleotide Transloase 1," *J. Biol. Chem.* Jan. 27, 2012, vol. 287, No. 5, 3573-3580.

Nagy et al., "Oxidized LDL Regulates Macrophage Gene Expression through Ligand Activation of PPARγ," *Cell* 1998, vol. 93, 229-240.

Napolitano et al., "The acid-promoted reaction of ethyl linoleate with nitrite. New insights from $^{15}$N-labelling and peculiar reactivity of a model skipped diene," *Tetrahedron* 2002, vol. 58, 5061-5067.

Napolitano et al., "Acid-Induced Structural Modifications of Unsaturated Fatty Acids and Phenolic Olive Oil Constituents by Nitrite Ions: A Chemical Assessment," *Chem. Res. Toxicol.* 2004, vol. 17, 1329-1337.

Narayan et al., "Serine Threonine Protein Kinases of Mycobacterial Genus: Phylogeny to Function," *Physiological Genomics* 2007, vol. 29, 66-75.

Nathan, "Nitric oxide as a secretory product of mammalian cells," *FASEB J.* 1992, vol. 6, 3051-3064.

Newman et al., "Optimized Thiol Derivatizing Reagent for the Mass Spectral Analysis of Distributed Epoxy Fatty Acids," *J. Chromato.* May 22, 2011, No. 925, 223-240.

Niebisch et al., "Corynebacterial Protein Kinase G Controls 2-Oxoglutarate Dehydrogenase Activity via the Phosphorylation Status of the Odh1 Protein," *J. Biolo. Chem.* 2006, vol. 281, No. 18, 12300-12307.

Notredame et al., "T-Coffee: A novel method for fast and accurate multiple sequence alignment," *J. Molec. Bio.* 2000, vol. 302, 205-217.

Nott et al., "An Intramolecular Switch Regulates Phosphoindependent FHA Domain Interactions in *Mycobacterium tuberculosis,*" *Sci. Signaling* 2009, vol. 2, No. 63, ra 12.

O'Donnell et al., "Interactions Between Nitric Oxide and Lipid Oxidation Pathways: Implications for Vascular Disease," *Circ. Res.* 2001, vol. 88, 12-21.

O'Donnell et al., "15-Lipoxygenase Catalytically Consumes Nitric Oxide and Impairs Activation of Guanylae Cyclase," *J. Biol. Chem.* Jul. 16, 1999, vol. 274, No. 29, 20083-20091.

O'Donnell et al., "Catalytic Consumption of Nitric Oxide by Prostagladin H Synthase-1 Regulates Platelet Function," *J. Biol. Chem.* Dec. 8, 2000, vol. 275, No. 49, 38239-38244.

O'Donnell et al., "Nitration of Unsaturated Fatty Acids by Nitric Oxide-Derived Reactive Nitrogen Species Peroxynitrite, Nitrous Acid, Nitrogen Dioxide, and Nitronium Ion," *Chem. Res. Toxicol.* 1999, vol. 12, No. 1, 83-92.

O'Donnell et al., "Nitric Oxide Inhibition of Lipid Peroxidation: Kinetics of Reaction with Lipid Peroxyl Radicals and Comparison with α-Tocopherol," *Biochem.* 1997, vol. 36, No. 49, 15216-15223.

Office Action issued on Nov. 21, 2013, for U.S. Appl. No. 13/387,489.

Office Action issued on Aug. 27, 2010, by the Japanese Patent Office in corresponding Japanese Patent Application No. 2014-186472, and a partial English Translation of the Office Action.

Office Action issued on Mar. 16, 2012, for corresponding foreign application, Chinese Patent Application No. 200980123324.1 (English translation).

Office Action issued on Oct. 10, 2011, for corresponding foreign application, Chinese Patent Application No. 200980127890.X (English translation).

Office Action issued on Jul. 7, 2012, for corresponding foreign application, Chinese Patent Application No. 200980127890.X (English translation).

Office Action issued on Apr. 1, 2013, for corresponding foreign application, Chinese Patent Application No. 200980127890.X (English translation).

Office Action issued on Oct. 31, 2013, for corresponding foreign application, Chinese Patent Application No. 200980127890.X (English translation).

Office Action issued on Jun. 5, 2014, for corresponding foreign application, Chinese Patent Application No. 200980127890.X (English translation).

Office Action issued on May 5, 2014, for corresponding foreign application CN201310054350.1 (English translation).

O'Hare et al., "Regulation of Glutamate Metabolism by Protein Kinases in Mycobacteria," *Mol. Microbio.* 2008, vol. 70, No. 6, 1408-1423.

Ortiz-Lombardia et al., "Crystal Structure of the Catalytic Domain of the PknB Serine/Threonine Kinase from *Mycobacterium tuberculosis,*" *J. Biolo. Chem.* 2003, vol. 278, No. 15, 13094-13100.

Padmaja et al., "The Reaction of Nitric Oxide With Organic Peroxyl Radicals," *Biochem. Biophys. Res. Commun.* 1993, vol. 195, No. 2, 539-544.

Park et al., "Modulation of Tumor Necrosis Factor-Related Apoptosis-Inducing Ligand-Induced Apoptosis by Chemotherapy in Thyroid Cancer Cell Lines," *Thyroid* 2003, vol. 13. No. 12, 1103-1110.

Pawliczak et al., "85-kDa Cytosolic Phospholipase $A_2$ Mediates Peroxisome Proliferator-activated Receptor γ Activation in Human Lung Epithelial Cells," *J. Biol. Chem.* 2002, vol. 277, 33153-33163.

Pryor et al., "Reaction of Nitrogen Dioxide with Alkenes and Polyunsaturated Fatty Acids: Addition and Hydrogen Abstraction Mechanisms," *J. Amer. Chem. Soc.* 1982, vol. 104, 6685-6692.

Quijano et al., "Reaction of Peroxynitrite with Mn-Superoxide Dismutase: Role of the Metal Center in Decomposition Kinetics and Nitration," *J. of Biol. Chem.* Apr. 13, 2001, vol. 276, No. 15, 11631-11638.

Radi et al., "Peroxynitrite Oxidation of Sulfhydryls: The Cytotoxic Potential of Superoxide and Nitric Oxide," *J. Biol. Chem.* 1991, vol. 266, No. 7, 4244-4250.

Radi et al., "Peroxynitrite Reactions with Carbon Dioxide-Bicarbonate," *Methods Enzymol.* 1999, vol. 301, No. 37, 353-367.

Ranu et al., "Highly Selective Reduction of Conjugated Nitroalkenes with Zinc Borohydride in DME," *Tetrahedron Letters* 1991, vol. 32, No. 29, 3579-3582.

Rassaf et al., "Concomitant Presence of N-Nitroso and S-Nitroso Proteins in Human Plasma," *Free Radic. Biol. Med.* 2002, vol. 33, No. 11, 1590-1596.

Rassaf et al., "NO adducts in mammalian red blood cells: too much or too little?" *Nat. Med.* 2003, vol. 9, No. 5, 481-482.

REMINGTON's *Pharmaceutical Sciences* 1990, 18th Ed. (TOC).

Rosen et al., "PPARγ: a Nuclear Regulator of Metabolism, Differentiation, and Cell Growth," *J. Biol. Chem.* 2001, vol. 276, No. 1, 37731-37734.

Rowe et al., "Acesulfame Potassium," *Handbook of Pharma. Excipients* 2006, $5^{th}$ Ed., Great Britain: Pharmaceutical Press (abstract).

Rubbo et al., "Form on Nitric Oxide: Chemical Events in Toxicity. Nitrix Oxide Regulation of Tissue Free Radical Injury," *Chem. Res. Toxicol.* 1996, vol. 9, No. 5, 809-820.

Rubbo et al., "Nitric Oxide Inhibition of Lipoxygenase-Dependent Liposome and Low-Density Lipoprotein Oxidation: Termination of Radical Chain Propagation Reactions and Formation of Nitrogen-Containing Oxidized Lipid Derivatives," *Arch. Biochem. Biophys.* Dec. 1, 1995, vol. 324, No. 1, 15-25.

Rubbo et al., "Nitric Oxide Reaction with Lipid Peroxyl Radicals Spares α-Tocopherol during Lipid Peroxidation," *J. Biol. Chem.* 2000, vol. 275, No. 25, 10812-10818.

Rubbo et al., "Nitric Oxide Regulation of Superoxide and Peroxynitrite-dependent Lipid Peroxidation," *J. Biol. Chem.* Oct. 21, 1994, vol. 269, No. 42, 26066-26075.

Rudnick et al., "Contrast-induced nephropathy: How it develops, how to prevent it," *Cleveland Clinic J. Med.* Jan. 2006, vol. 73, No. 1, 75-87.

(56) References Cited

OTHER PUBLICATIONS

Rudolph et al., "Cardiovascular Consequences When Nitric Oxide and Lipid Signaling Converge," *Circ. Res.* Sep. 11, 2009, vol. 105, 511-522.
Rudolph et al., "Endogenous generation and protective effects of nitro-fatty acids in murine model of focal cardiac ischaemia and reperfusion," *Cardiov. Res. Advance Access* 2009, 1-12.
Rudolph et al., "Nitro-fatty Acid Metabolome: Saturation, Desaturation, β-Oxidation, and Protein Adduction," *J. Biol. Chem.* Jan. 16, 2009, vol. 284, No. 3, 1461-1473.
Rudolph et al., "Nitro-Fatty Acids Reduce Atherosclerosis in Apolipoprotein E-Deficient Mice," *Ather. Thromb. Vasc. Bio.* May 2010, vol. 30, 938-945.
Rudolph et al., "Transduction of Redox Signaling by Electrophile-Protein Reactions," *Sc. Signaling* Sep. 29, 2009, vol. 2, Issue 90 re7, 1-13.
Ryan et al., "Diabetes and the Mediterranean Diet: a Beneficial Effect of Oleic Acid on Insulin Sensitivity, Adipocyte Glucose Transport and Endothelium-dependent Vasoreactivity," *Q. J. Med.* 2000, vol. 93, 85-91.
Saffer et al., "Choosing Drug Therapy for Patients with Hyperlipidemia," *Am. Fam. Physic.* Jun. 1, 2000, vol. 61, No. 11, 3371-3382.
Sarver et al., "Analysis of Peptides and Proteins Containing Nitrotyrosine by Matrix-assisted Laser Desorption/ionization Mass Spectrometry," *J. Am. Soc. Mass Spectrom.* 2001, vol. 12, No. 4, 439-448.
Satyanarayana et al., "Steroselective Synthesis of Diacids by the Nickel Cyanide and Phase-Transfer-Catalyzed Carbonylation of Alkynols. Novel Dependency of Product Stereochemistry and Optimum Stirring Speed on the Nature of the Phase-Transfer Agent," *Organometallics* 1991, vol. 10, 804-807.
Saulnier-Blache et al., "A simple and highly sensitive radioenzymatic assay for lysophosphatidic acid quantification," *J. Lipid Res.* 2000, vol. 41, 1947-1951.
Scherr et al., "Structural Basis for the Specific Inhibition of Protein Kinase G, a Virulence Factor of *Mycobacterium tuberculosis*," *PNAS* 2007, vol. 104, No. 29, 12151-12156.
Schopfer et al., "Fatty Acid Transduction of Nitric Oxide Signaling. Nitrolinoleic Acid is a Hydrophobically Stabilized Nitric Oxide Donor," *J. Biol. Chem.* May 13, 2005, vol. 280, No. 19, 19289-19297.
Schopfer et al., "Nitrolinoleic Acid: An endogenous peroxisome proliferator-activated receptor γ ligand," *Proc. Natl. Acad. Sci.* Feb. 15, 2005, vol. 102(7), 2340-2345.
Schopfer et al., "NO-dependent protein nitration: a cell signaling event or an oxidative inflammatory response?" *Trends Biochem. Sci.* 2003, vol. 28, 646-654.
Schopfer et al., "Covalent Peroxisome Proliferator-activated Receptor γ Adduction by Nitro-fatty Acids: Selective ligand activity and anti-diabetic signaling actions," *J. Biol. Chem.* Apr. 16, 2010, vol. 285, No. 16, 12321-12333.
Schopfer et al., "Detection and quantification of protein adduction by electrophilic fatty acids: mitochondrial generation of fatty acid nitroalkene derivatives," *Free Radic. Biol. Med.* 2009, vol. 46, 1250-1259.
Sculptoreanu et al., "Nitro-Oleic Acid Inhibits Firing and Activates TRPV-1 and TRPA1-Mediated Inward Currents in Dorsal Root Ganglion Neurons from Adult Male Rats," *J. Pharm. Expt. Thera.* 2010, vol. 333, No. 3, 883-895.
Serhan et al., "Anti-Inflammatory Actions of Neuroprotectin D1/Protectin D1 and Its Natural Stereoisomers: Assignments of Dihydroxy-Containing Docosatrienes," *J. Immunology* 2006, vol. 176, 1848-1859.
Setiadi et al., "Vitamin E models. Conformational analysis and stereochemistry of tetralin, choman, thiochroman and selenochroman," *J. Molecular Structure (Theochem)* 2002, vol. 594, 161-172.
Shaner et al., "Designing Herbicide Tolerance Based on Metabolic Alteration: the Challenges and the Future," In *Pesticide Biotransformation in Plants and Microorganisms* (Hall, J. et al.); ACS Symposium Series 2000, American Chemical Society; Washington DC.
Sieker et al., "Rubredoxin in Crystalline State," *Methods Enzymol.* 1994, vol. 243, 203-216.
Smith, "Prostanoid biosynthesis and mechanisms of action," *Am. Physiol. Soc.* 1992, vol. 263, F181-F191.
Snider et al., "Oxidative and Dehydrative Cyclizations of Nitroacetate Esters with $Mn(Oac)_3$," *Tetrahedron*, Sep. 23, 2002, vol. 58, No. 39, 7821-7827.
Söding et al., "HHsenser: Exhaustive Transitive Profile Search Using HMM-HMM Comparison," *Nucleic Acids Res.* 2006, vol. 34, W374-378.
Strowig et al., "Combination therapy using metformin or thiazolidinediones and insulin in the treatment of diabetes mellitus," *Diabetes, Obesity, and Metabolism* 2005, vol. 7, 633-641.
Subczynski et al., "Permeability of Nitric Oxide through Lipid Bilayer Membranes," *Free Radic. Res.* 1996, vol. 24, 343-349.
Summons to Attend Oral Proceedings dated Oct. 2, 2012, from corresponding European Patent Application No. 08780348.2.
Szekely et al., "A Novel Drug Discovery Concept for Tuberculosis. Inhibition of Bacterial and Host Cell Signaling," *Immun. Letters* 2008, vol. 116, No. 2, 225-231.
Szoka et al., "Comparative Properties and Methods of Preparation of Lipid Vesicles (Liposomes)," *Annu. Rev. Biophys. Bioeng.* 1980, vol. 9, 467-508.
Tang et al., "Nitroalkenes induce rat aortic smooth muscle cell apoptosis via activation of caspase-dependent pathways," *Biochem. Biophys. Res. Commun.* 2010, vol. 397, 239-244.
Thatcher et al., "Nitrates and no Release: Contemporary Aspects in Biological and Medicinal Chemistry," *Free Radic. Biol. Med.* 2004, vol. 37, No. 8, 1122-1143.
Thomas et al., "The biological lifetime of nitric oxide. Implications for the perivascular dynamics of NO and $O_2$," *Proc. Natl. Acad. Sci.* Jan. 2, 2001, vol. 98, No. 1, 355-360.
Tiwari et al., "Key Residues in *Mycobacterium tuberculosis* Protein Kinase G Play a Role in Regulating Kinase Activity and Survival in the Host," *J. Biolol. Chem.* 2009, vol. 284, No. 40, 27467-27479.
Tontonoz et al., "Stimulation of Adipogenesis in Fibroblasts by PPARγ2, a Lipid-Activated Transcription Factor," *Cell* 1994, vol. 79, 1147-1156.
Tontonoz et al., "mPPARγ2: tissue-specific regulator of an adipocyte enhancer," *Genes Dev.* 1994, vol. 8, No. 10, 1224-1234.
Toth, "High-Density Lipoprotein and Cardiovascular Risk," *Circulation* 2004, vol. 109, 1809-1812.
Tsikas et al., "Nitro-fatty Acids Occur in Human Plasma in the Picomolar Range: a Targeted Nitro-lipidomics GC-MS/MS Study," *Lipids* 2009, vol. 44, 855-865.
Tzameli et al., "Regulated Production of a Peroxisome Proliferatory-Activated Receptor-gamma Ligand during an Early Phase of Adipocyte Differentiation in 3T3-L1 Adipocytes," *J. Biol. Chem.* 2004, vol. 279, No. 34, 36093-36102.
U.S. Appl. No. 13/646,985, Non-Final Office Action mailed Jun. 12, 2014.
U.S. Appl. No. 13/646,985, Non-Final Office Action mailed May 1, 2014.
U.S. Appl. No. 13/646,985, Notice of Allowance, Dec. 5, 2014.
U.S. Appl. No. 14/638,370, Non-Final Office Action, Jul. 8, 2015.
U.S. Appl. No. 14/638,370, Notice of Allowance, Nov. 18, 2015.
Van Beilen et al., "Rubredoxins Involved in Alkane Oxidation," *J. Biolol. Chem.* 2002, vol. 184, No. 6, 1722-1732.
Vickers et al., "IGF-1 Treatment Reduces Hyperphagia, Obesity, and Hypertension in Metabolic Disorders Induced by Fetal Programming,"*Endocrinol.* Sep. 2001, vol. 142, No. 9, 3964-3973.
Vidwans et al., "Differential Modulation of Prostaglandin H Synthase-2 by Nitric Oxide-Related Species in Intact Cells," *Biochem.* 2001, vol. 40, 11533-11542.
Villacorta et al., "Nitro-linoleic Acid Inhibits Vascular Smooth Muscle Cell Proliferation via the Keap1/Nrf2 Signaling Pathway," *Am. J. Physiol. Heart Circ. Physiol.* Apr. 27, 2007, 1-9.
Villacorta et al., "PPARγ and its ligands: therapeutic implications in cardiovascular disease," *Clin. Sci.* 2009, vol. 116, 205-218.

(56) References Cited

OTHER PUBLICATIONS

Villarino et al., "Proteomic Identification of M. Tuberculosis Protein Kinase Substrates: PknB Recruits GarA, a FHA Domain-containing Protein, Through Activation Loop-mediated Interactions," *J. Mol. Bio.* 2005, vol. 350, No. 5, 953-963.
'Virtual Chembook' in www.elmhurst.edu/~chm/vchembook/551fattyacids.html (retrieved Dec. 12, 2012).
Von Knethen et al., "Activation of Peroxisome Proliferator-Activated Receptor γ by Nitric Oxide in Monocytes/Macrophages Down-Regulates p47$^{phox}$ and Attenuates the Respiratory Burst," *J. Immunol.* 2002, vol. 169, 2619-2626.
Walburger et al., "Protein Kinase G from Pathogenic Mycobacteria Promotes Survival Within Macrophages," *Sci.* 2004, vol. 304, 1800-1804.
Wang et al., "Constitutive Activation of Peroxisome Proliferator-activated Receptor-γ Suppresses Pro-inflammatory Adhesion Molecules in Human Vascular Endothelial Cells," *J. Biol. Chem.* 2002, vol. 277, No. 37, 34176-34181.
Wang et al., "Effects of Endogenous PPAR Agonist Nitro-Oleic Acid on Metabolic Syndrome in Obese Zucker Rats," *PPAR Res.* 2010, vol. 2010, Art. ID 601562, 1-7.
Wang et al., "Nitro-oleic acid protects against endotoxin-induced endotoxemia and multiorgan injury in mice," *Am. J. Physiol. Renal Physiol.* Dec. 23, 2009, vol. 298, F754-762.
Weber et al., "Fragmentation of Bovine Serum Albumin by Pepsin. 1. The Origin of the Acid Expansion of the Albumin Molecule," *J. Biolo. Chem.* 1964, vol. 239, No. 5, 1415-1423.
Wehenkel et al., "Mycobacterial Ser/Thr Protein Kinases and Phosphatases: Physiological Roles and Therapeutic Potential," *Biochemica et biophysica acta* 2008, vol. 1784, No. 1, 193-202.
Wright et al., "Fatty acid transduction of nitric oxide signaling: Nitrolinoleic acid potently activates endothelial heme oxygenase 1 expression," *PNAS* Mar. 14, 2006, vol. 103, No. 11, 4299-4304.
Wright et al., "Human Heme Oxygenase-1 Induction by Nitrolinoleic Acid is Mediated by cyclic AMP, AP-1, and E-box Response Element Interactions," *Biochem. J.* 2009, m. BJ20090339, 1-31.
Written Opinion issued in corresponding PCT/US2012/059722, 1-8 (Aug. 19, 2013).
Xu et al., "Lysophosphatidic Acid as a Potential Biomaker for Ovarian and Other Gynecologic Cancers," *JAMA* 1998, vol. 280, 719-723.
Zhang et al., "Lysophosphatidic Acid Induces Neointima Formation Through PPARgamma Activation," *J. ExMed.* 2004, vol. 199, No. 6, 763-774.
Zhang et al., "Selective disruption of PPARgamma2 impairs the development of adipose tissue and insulin sensitivity," *Proc. Natl. Acad. Sci.* 2004, vol. 101, No. 29, 10703-10708.
Zhang et al., "Nitro-Oleic Acid Inhibits Angiotensin II-Induced Hypertension," *Circ. Res.* 2010, vol. 107, 540-548.
Dembitsky et al., "Natural halogenated fatty acids: their analogues and derivatives," *Progress in Lipid Research* 2002, vol. 41, No. 4, 315-367.
Duan et al., "Nephrotoxicity of high- and low-osmolar contrast media: Protective role of forsinopril or telmisartan in a rat model," *J. Central S. Univ.* (Dec. 31, 2007), vol. 32, No. 5, 812-818.
Extended European Search Report and Written Opinion issued in corresponding European Patent Application No. 16157509.7, 1-9 (May 30, 2016).
Office Action issued in corresponding foreign application CN201310054350.1, 1-3 (Jan. 13, 2015).
Bervejillo et al., "Estudio del Potencial Anti-Aterogenico del AANO$_2$ in Vivo," *Tesina del grado de la Licenciatura en Bioquiica, Facultad de Ciencias,* UdelR Feb. 5-6, 2012, Fig. 2.
Kim et al., "The effect of PPAR-γ agonist on glucose metabolism and insulin sensitivity in on-obese type 2 diabetic rat models," *Diabetes* Jun. 1, 2006, American Diabetes Association 55:Suppl. 1.
Nagano et al., "Use of tacrolimus, a potent antifibrotic agent, in bleomycin-induced lung fibrosis," *Eur. Respir. J.* 2006, vol. 27, 460-469.
*Pharma Medica* (2002), 20(5):1999-210 (in Japanese with brief English relevance).
Vasil'ev et al., "The action of nitrogen dioxide upon erucic acid," *Lomonosova* 1995, vol. 5, 50-58.
Cha et al., "Peroxisome Proliferator-Activated Receptor α/γ Dual Agonist Tesaglitazar Attenuates Diabetic Nephropathy in db/db Mice," *Diabetes* (Aug. 2007), 56(8):2036-2045.
Yamamoto et al., "Identification of putative metabolites of docosahexaenoic acid as potent PPARγ agonists and antidiabetic agents," *Bioorgan. Medicinal Chem. Ltrs,* 2005, 15:517-522.

* cited by examiner

HETEROATOM CONTAINING SUBSTITUTED FATTY ACIDS

CROSS-REFERENCE TO RELATED APPLICATIONS

This application is a continuation of U.S. application Ser. No. 12/896,039 filed Oct. 1, 2010, which claims the benefit of priority to U.S. Provisional Patent Application No. 61/248,049 filed Oct. 2, 2009, all of which are incorporated herein as references in their entireties.

BRIEF SUMMARY OF THE INVENTION

Embodiments of the invention are directed to compounds including a naturally or non-naturally occurring, unsaturated or polyunsaturated fatty acid having one or more electron withdrawing group wherein at least one electron withdrawing group is associated with a carbon-carbon double bond or a heteroatom or a pharmaceutically acceptable salt thereof. In some embodiments, the naturally or non-naturally occurring, unsaturated or polyunsaturated fatty acid may include an aliphatic chain having an number of carbons from about 4 to about 25, and in other embodiments, the naturally or non-naturally occurring, unsaturated or polyunsaturated fatty acid may include an aliphatic chain having 4 to 23 carbons or, in certain embodiments, an aliphatic chain having 4, 5, 6, 7, 8, 9, 10 11, 12, 13, 14, 15, 16, 17, 18, 19, 20, 21, 22, 23, 24, or 25 carbons. In additional embodiments, the naturally or non-naturally occurring unsaturated or polyunsaturated fatty acid may be a glycolipid, a glycerolipid, a phospholipid and a cholesterol ester.

The one or more electron withdrawing group of various embodiments may include, but are not limited to, aldehyde (—COH), acyl (—COR), carbonyl (—CO), carboxylic acid (—COOH), ester (—COOR), halides (—Cl, —F, —Br, —I), fluoromethyl allyl fluoride (—CH═CHCH$_2$F), cyano (—CN), sulfoxide (—SOR), sulfonyl (—SO$_2$R), sulfonic acid (—SO$_3$H), 1°, 2° and 3° ammonium (—NR$_3^+$), or nitro (—NO$_2$), wherein R is a hydrogen, methyl or C$_2$-C$_6$ alkyl, and in particular embodiments, the one or more electron withdrawing group may be a nitro (—NO$_2$) group. In some embodiments, the one or more electron withdrawing group may be positioned on an alpha carbon of a carbon-carbon double bond of the naturally or non-naturally occurring, unsaturated or polyunsaturated fatty acid, and in other embodiments, the one or more electron withdrawing group may be positioned on a beta carbon of a carbon-carbon double bond of the naturally or non-naturally occurring, unsaturated or polyunsaturated fatty acid. In still other embodiments, the one or more electron withdrawing group may be positioned on a gamma carbon of a carbon-carbon double bond of the naturally or non-naturally occurring, unsaturated or polyunsaturated fatty acid. In certain embodiments, the at least one of the one or more electron withdrawing group may be an electron withdrawing vinyl group or an electron withdrawing allylic group. In some embodiments, a carbon-carbon double bond associated with the one or more electron withdrawing group may be in cis configuration, and in others, a carbon-carbon double bond associated with the one or more electron withdrawing group may be in trans configuration. In still other embodiments, the one or more electron withdrawing group may be in an absolute stereochemistry of R at an sp$^3$ chiral/stereogenic center, and in some other embodiments, the one or more electron withdrawing group may be in an absolute stereochemistry of S at an sp$^3$ chiral/stereogenic center.

In various embodiments, a carbon-carbon double bond may occur at any carbon of the aliphatic chain of the naturally or non-naturally occurring, unsaturated or polyunsaturated fatty acid. In some embodiments, the naturally or non-naturally occurring, unsaturated or polyunsaturated fatty acid may be a fatty acid with two or more conjugated carbon-carbon double bonds, and in particular embodiments, at least one of the one or more electron withdrawing group may be at any carbon in the two or more conjugated carbon-carbon double bonds. In certain embodiments, at least one of the one or more electron withdrawing group may be positioned at C-9, C-10, C-12, C-13 or a combination thereof.

In various embodiments, one or more heteroatoms may be positioned anywhere on the aliphatic chain of the unsaturated or polyunsaturated fatty acid, and in some embodiments, at least one heteroatom may be positioned at the first 1, 2, 3, or 4 carbons from the carboxy terminus of the fatty acid to produce a carbonate, acetic acid, propionic acid, or butanoic acid derivatives of the activated fatty acid. In other embodiments, an electron withdrawing group may be positioned at a carbon immediately adjacent to the heteroatom, or in further embodiments, the carbon immediately adjacent to the carbon immediately adjacent to the heteroatom. In still other embodiments, an electron withdrawing group may be positioned at both carbons immediately adjacent to the heteroatom, and/or the carbon immediately adjacent to the carbon immediately adjacent to the heteroatom. In yet other embodiments, there may be no electron withdrawing associated with the heteroatom provided that the aliphatic chain include at least one electron withdrawing group associated with another heteroatom or a carbon-carbon double bond.

In some embodiments, one or more non-carbon-carbon linkage such as, for example, an ester linkage, an ether linkage, and a vinyl ether linkage may be substituted on the aliphatic chain of the naturally or non-naturally occurring, unsaturated or polyunsaturated fatty acid, and in other embodiments, the naturally or non-naturally occurring, unsaturated or polyunsaturated fatty acid may further include one or more functional group other than an electron withdrawing group positioned at any carbon of the aliphatic chain of the naturally or non-naturally occurring, unsaturated or polyunsaturated fatty acid.

In particular embodiments, the composition can further include a pharmaceutically acceptable carrier or excipient. In other embodiments, the composition may further include one or more of diluents, fillers, disintegrants, binders, lubricants, surfactants, hydrophobic vehicles, water soluble vehicles, emulsifiers, buffers, humectants, moisturizers, solubilizers, antioxidants, preservatives or combinations thereof, and in still other embodiments, compound may further including a pharmaceutically acceptable carrier or excipient may be formulated as, for example, a solid, solution, powder, fluid emulsion, fluid suspension, semi-solid or dry powder.

Various embodiments of the invention further include a compound comprising an unsaturated or polyunsaturated fatty acid having at least one heteroatom and/or at least one carbon-carbon double bond and one or more electron withdrawing group associated with at least one heteroatom or double bond or a pharmaceutically acceptable salt thereof, with the proviso that the electron withdrawing group associated with the at least one double bond is not a nitro (—NO$_2$) group. In some embodiments, the unsaturated or polyunsaturated fatty acid may include a naturally occurring fatty acid or derivative thereof, and in such embodiments, the unsaturated or polyunsaturated fatty acid may include an aliphatic carbon chain having an even number of carbons. In particular embodiments, the unsaturated or polyunsaturated fatty acid may include an aliphatic carbon chain having from 4 to 24 carbons, and in other embodiments, the unsaturated or polyunsaturated fatty acid comprises an aliphatic carbon chain having from 12 to 18 carbons. In certain embodiments, the unsaturated or polyunsaturated fatty acid may be, for example, a ω-2, ω-3, ω-4, ω-5, ω-6, ω-7, ω-8, ω-9 fatty acids and equivalents and derivatives thereof. For example, in some embodiments, the unsaturated or polyunsaturated fatty acid may be linolenic acid, alpha-linolenic acid, eicosapentanoic acid, docosapentaenoic acid, docosahexaenoic acid, stearidonic acid, myristoleic acid, linoleic acid, gamma-linoleic acid, dihomo-gamma-linoleic acid, arachidonic acid, palmitoleic acid, oleic acid, erucic acid and equivalents and derivatives thereof, and in other embodiments, the unsaturated fatty acid is selected from linoleic acid, oleic acid, arachidonic acid or a derivative thereof. In still other embodiments, the unsaturated or polyunsaturated fatty acid may be, for example, a glycolipid, a glycerolipid, a phospholipid and a cholesterol ester.

In some embodiments, the at least one electron withdrawing group may be positioned at C-9, C-10, C-12, C-13 or a combination thereof, and in other embodiments, the unsaturated or polyunsaturated fatty acid may include one or more non-carbon-carbon linkage selected from an ester linkage, an ether linkage, a vinyl ether linkage or a combination thereof.

In various embodiments, the one or more electron withdrawing group may be, for example, aldehyde (—COH), acyl (—COR), carbonyl (—CO), carboxylic acid (—COOH), ester (—COOR), halides (—Cl, —F, —Br, —I), fluoromethyl (—$CF_n$) allyl fluoride (—CH=$CHCH_2F$), cyano (—CN), sulfoxide (—SOR), sulfonyl (—$SO_2R$), sulfonic acid (—$SO_3H$), and 1°, 2° and 3° ammonium (—$NR_3^+$), wherein R is a hydrogen, methyl or $C_2$-$C_6$ alkyl. In some embodiments, the one or more electron withdrawing group may be positioned on an alpha carbon of a carbon-carbon double bond of the unsaturated or polyunsaturated fatty acid. In other embodiments, the one or more electron withdrawing group may be positioned on a beta carbon of a carbon-carbon double bond of the unsaturated or polyunsaturated fatty acid, and in still other embodiments, the one or more electron withdrawing group is positioned on a gamma carbon of a carbon-carbon double bond of the unsaturated or polyunsaturated fatty acid. In yet other embodiments, the at least one of the one or more electron withdrawing group may be an electron withdrawing vinyl group or an electron withdrawing allylic group.

In certain embodiments, a carbon-carbon double bond associated with the one or more electron withdrawing group may be in cis configuration, and in some embodiments, a carbon-carbon double bond associated with the one or more electron withdrawing group may be in trans configuration. In other embodiments, the one or more electron withdrawing group may be in an absolute stereochemistry of R at an $sp^3$ chiral/stereogenic center, and in still other embodiments, the one or more electron withdrawing group may be in an absolute stereochemistry of S at an $sp^3$ chiral/stereogenic center.

A carbon-carbon double bond may occur at any carbon of the aliphatic chain of the naturally occurring, unsaturated or polyunsaturated fatty acid in various embodiments, of the invention. In some embodiments, the unsaturated or polyunsaturated fatty acid may be a fatty acid with two or more conjugated carbon-carbon double bonds, and in other embodiments, at least one of the one or more electron withdrawing group may be at any carbon in the two or more conjugated carbon-carbon double bonds.

In particular embodiments, the unsaturated or polyunsaturated fatty acid having one or more electron withdrawing group associated with at least one double bond or a pharmaceutically acceptable salt thereof may further include a pharmaceutically acceptable carrier or excipient. In some embodiments, the unsaturated or polyunsaturated fatty acid having one or more electron withdrawing group associated with at least one double bond or a pharmaceutically acceptable salt thereof may further include one or more of diluents, fillers, disintegrants, binders, lubricants, surfactants, hydrophobic vehicles, water soluble vehicles, emulsifiers, buffers, humectants, moisturizers, solubilizers, antioxidants, preservatives or combinations thereof, and in other embodiments, the unsaturated or polyunsaturated fatty acid having one or more electron withdrawing group associated with at least one double bond or a pharmaceutically acceptable salt thereof further including a pharmaceutically acceptable carrier or excipient may be formulated as a solid, solution, powder, fluid emulsion, fluid suspension, semi-solid or dry powder.

Some embodiments of the invention are directed to a method for treating a condition by administering an effective amount of an unsaturated or polyunsaturated fatty acid having one or more electron withdrawing group associated with at least one double bond with the proviso that the electron withdrawing group is not nitro (—$NO_2$) or a pharmaceutically acceptable salt thereof to a subject in need of treatment. In such embodiments, the one or more electron withdrawing group is selected from aldehyde (—COH), acyl (—COR), carbonyl (—CO), carboxylic acid (—COOH), ester (—COOR), halides (—Cl, —F, —Br, —I), fluoromethyl ($CF_n$) allyl fluoride (—CH=$CHCH_2F$), cyano (—CN), sulfoxide (—SOR), sulfonyl (—$SO_2R$), sulfonic acid (—$SO_3H$), and 1°, 2°, and 3° ammonium (—$NR_3^+$), wherein R is a hydrogen, methyl or $C_2$-$C_6$ alkyl. In some embodiments, the unsaturated or polyunsaturated fatty acid may include an aliphatic carbon chain having from 12 to 18 carbons, and in other embodiments, the unsaturated or polyunsaturated fatty acid may be a ω-2, ω-3, ω-4, ω-5, ω-6, ω-7, ω-8, or ω-9 fatty acids and equivalents and derivatives thereof. For example in certain embodiments, the unsaturated or polyunsaturated fatty acid may be linolenic acid, alpha-linolenic acid, eicosapentanoic acid, docosapentaenoic acid, docosahexaenoic acid, stearidonic acid, myristoleic acid, linoleic acid, gamma-linoleic acid, dihomo-gamma-linoleic acid, arachidonic acid, palmitoleic acid, oleic acid, erucic acid and equivalents and derivatives thereof.

In other embodiments, the one or more electron withdrawing group may be positioned on an alpha carbon of a carbon-carbon double bond of the unsaturated or polyunsaturated fatty acid. In other embodiments, the one or more electron withdrawing group may be positioned on a beta carbon of a carbon-carbon double bond of the unsaturated or polyunsaturated fatty acid, and in still other embodiments, the one or more electron withdrawing group may be positioned on a gamma carbon of a carbon-carbon double bond of the unsaturated or polyunsaturated fatty acid. In particular embodiments, at least one of the one or more electron withdrawing group may be an electron withdrawing vinyl group or an electron withdrawing allylic group. In some embodiments, a carbon-carbon double bond associated with the one or more electron withdrawing group may be in cis configuration, and in other embodiments, a carbon-carbon double bond associated with the one or more electron withdrawing group may be in trans configuration. In certain embodiments, the effective amount may include a mixture of unsaturated or polyunsaturated fatty acids having one or more electron withdrawing group associated with at least one double bond wherein the mixture includes electron withdrawing group positioned on alpha, beta, and gamma carbon of a carbon-carbon double bonds of the unsaturated or polyunsaturated fatty acids.

In various embodiments, the condition may be, but may not be limited to, arterial stenosis, burns, hypertension, obesity, neurodegenerative disorders, skin disorders, arthritis, autoimmune disease, autoinflammatory disease, lupus, Lyme's disease, gout, sepsis, hyperthermia, ulcers, enterocolitis, osteoporosis, viral or bacterial infections, cytomegalovirus, periodontal disease, glomerulonephritis, sarcoidosis, lung disease, chronic lung injury, respiratory distress, lung inflammation, fibrosis of the lung, asthma, acquired respiratory distress syndrome, tobacco induced lung disease, granuloma formation, fibrosis of the liver, graft vs. host disease, postsurgical inflammation, coronary and peripheral vessel restenosis following angioplasty, stent placement or bypass graft, acute and chronic leukemia, B lymphocyte leukemia, neoplastic diseases, arteriosclerosis, atherosclerosis, myocardial inflammation, psoriasis, immunodeficiency, disseminated intravascular coagulation, systemic sclerosis, amyotrophic lateral sclerosis, multiple sclerosis, Parkinson's disease, Alzheimer's disease, encephalomyelitis, edema, inflammatory bowel disease, hyper IgE syndrome, cancer metastasis or growth, adoptive immune therapy, reperfusion syndrome, radiation burns, and alopecia.

Other embodiments of the invention are directed to a method for treating a condition comprising administering an effective amount of a naturally or non-naturally occurring, unsaturated or polyunsaturated fatty acid having one or more electron withdrawing group, at least one heteroatom and/or at least one carbon-carbon double bond or a pharmaceutically acceptable salt thereof to a subject in need of treatment. In some embodiments, the condition may include, but may not be limited to arterial stenosis, burns, hypertension, obesity, neurodegenerative disorders, skin disorders, arthritis, autoimmune disease, autoinflammatory disease, lupus, Lyme's disease, gout, sepsis, hyperthermia, ulcers, enterocolitis, osteoporosis, viral or bacterial infections, cytomegalovirus, periodontal disease, glomerulonephritis, sarcoidosis, lung disease, chronic lung injury, respiratory distress, lung inflammation, fibrosis of the lung, asthma, acquired respiratory distress syndrome, tobacco induced lung disease, granuloma formation, fibrosis of the liver, graft vs. host disease, postsurgical inflammation, coronary and peripheral vessel restenosis following angioplasty, stent placement or bypass graft, acute and chronic leukemia, B lymphocyte leukemia, neoplastic diseases, arteriosclerosis, atherosclerosis, myocardial inflammation, psoriasis, immunodeficiency, disseminated intravascular coagulation, systemic sclerosis, amyotrophic lateral sclerosis, multiple sclerosis, Parkinson's disease, Alzheimer's disease, encephalomyelitis, edema, inflammatory bowel disease, hyper IgE syndrome, cancer metastasis or growth, adoptive immune therapy, reperfusion syndrome, radiation burns, and alopecia.

Various embodiments of the invention are directed to a pharmaceutical composition that may include any of the naturally or non-naturally occurring, unsaturated or polyunsaturated fatty acid having one or more electron withdrawing group, at least one heteroatom and/or at least one carbon-carbon double bond or a pharmaceutically acceptable salt thereof described herein and a pharmaceutically acceptable carrier or excipient. In some embodiments, such pharmaceutical compositions may further include one or more of diluents, fillers, disintegrants, binders, lubricants, surfactants, hydrophobic vehicles, water soluble vehicles, emulsifiers, buffers, humectants, moisturizers, solubilizers, antioxidants, preservatives or combinations thereof. In other embodiments, the pharmaceutical composition may be formulated as, for example, a solid, solution, powder, fluid emulsion, fluid suspension, semi-solid or dry powder.

Yet other embodiments of the invention include methods for preparing a naturally or non-naturally occurring, unsaturated or polyunsaturated fatty acid having one or more electron withdrawing group, at least one heteroatom and/or at least one carbon-carbon double bond or a pharmaceutically acceptable salt thereof.

DETAILED DESCRIPTION

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient, whereby the therapeutic positively impacts the tissue to which it is targeted. Thus, as used herein, the term "administering", when used in conjunction with a nitrated lipid can include, but is not limited to, providing a nitrated lipid to a subject systemically by, for example, intravenous injection, whereby the therapeutic reaches the target tissue. "Administering" a composition may be accomplished by, for example, injection, oral administration, topical administration, or by these methods in combination with other known techniques. Such combination techniques include heating, radiation, ultrasound and the use of delivery agents.

The term "animal" as used herein includes, but is not limited to, humans and non-human vertebrates such as wild, domestic and farm animals.

The term "improves" is used to convey that the present invention changes either the characteristics and/or the physical attributes of the tissue to which it is being provided, applied or administered. The term "improves" may also be used in conjunction with a diseased state such that when a diseased state is "improved" the symptoms or physical characteristics associated with the diseased state are diminished, reduced or eliminated.

The term "inhibiting" includes the administration of a compound of the present invention to prevent the onset of the symptoms, alleviating the symptoms, or eliminating the disease, condition or disorder.

By "pharmaceutically acceptable", it is meant the carrier, diluent or excipient must be compatible with the other ingredients of the formulation and not deleterious to the recipient thereof.

As used herein, the term "therapeutic" means an agent utilized to treat, combat, ameliorate, prevent or improve an unwanted condition or disease of a patient. In part, embodiments of the present invention are directed to the treatment of inflammation, obesity-related diseases, metabolic diseases, cardiovascular diseases, cerebrovascular and neurodegenerative diseases, cancer or the aberrant proliferation of cells.

A "therapeutically effective amount" or "effective amount" of a composition is a predetermined amount calculated to achieve the desired effect, i.e., to inhibit, block, or reverse the activation, migration, or proliferation of cells. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the effective amount administered will be determined by the physician in the light of the relevant circumstances including the condition to be treated, the choice of compound to be administered, and the chosen route of administration, and therefore, the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

Generally speaking, the term "tissue" refers to any aggregation of similarly specialized cells which are united in the performance of a particular function.

Nitric oxide (NO) is an endogenously generated, lipophilic signaling molecule that has been implicated in the maintenance of vascular homeostasis, modulation of oxygen radical reactions, inflammatory cell function, post-translational protein modification and regulation of gene expression. In addition, nitric oxide-derived species display separate and unique pharmacological properties, specifically can mediate oxidation and nitration of biomolecules such as, for example, unsaturated fatty acids.

Various reactions yield products capable of concerted oxidation, nitrosation and nitration of target molecules. For example, nitric oxide may react with superoxide ($O_2^-$) to yield peroxynitrite ($ONOO^-$) and its conjugate acid, peroxynitritrous acid ($ONOOH$), the latter of which may undergo homolytic scission to form nitrogen dioxide ($.NO_2$) and hydroxyl radical ($.OH$). In some instances, biological conditions may favor the reaction of $ONOO^-$ with $CO_2$ which yields nitrosoperoxycarbonate ($ONOOCO_2^-$), which rapidly yields $.NO_2$ and carbonate ($.CO_3^-$) radicals via homolysis or rearrangement to $NO_3^-$ and $CO_2$. During inflammation, neutrophil myeloperoxidase and heme proteins such as myoglobin and cytochrome c catalyze $H_2O_2$-dependent oxidation of nitrite ($NO_2^-$) to $.NO_2$, resulting in biomolecule oxidation and nitration that is influenced by the spatial distribution of catalytic heme proteins. The reaction of $.NO$ with $O_2$ can also produce products that can be substrates or reactants for nitrosation and nitration. For example, the small molecular radius, uncharged nature and lipophilicity of $.NO$ and $O_2$ facilitate concentration of these species in biological membranes in a process referred to as the "molecular lens" effect. The increase in concentration induced by $.NO$ and $O_2$ solvation in hydrophobic cell compartments accelerates the normally slow reaction of $.NO$ with $O_2$ to yield $N_2O_3$ and $N_2O_4$. Finally, environmental sources also yield $.NO_2$ as a product of photochemical air pollution and tobacco smoke.

Nitration of fatty acids by $.NO_2$ can occur through several methods. For example, during both basal cell signaling and tissue inflammatory conditions, $.NO_2$ can react with membrane and lipoprotein lipids. In both in vivo and in vitro systems, $.NO_2$ has been shown to initiate radical chain auto-oxidation of polyunsaturated fatty acids via hydrogen abstraction from the bis-allylic carbon to form nitrous acid and a resonance-stabilized bis-allylic radical. Depending on the radical environment, the lipid radical species can react with molecular oxygen to form a peroxyl radical, which can react further to form lipid hydroperoxides then oxidized lipids. During inflammation or ischemia, when $O_2$ levels are lower, lipid radicals can react to an even greater extent with $.NO_2$ to generate multiple nitration products including singly nitrated, nitrohydroxy- and dinitro-fatty acid adducts. These products can be generated via hydrogen abstraction, direct addition of $.NO_2$ across the double bond, or both, and in some cases, such reactions may be followed by further reactions of the intermediate products that are formed. Hydrogen abstraction causes a rearrangement of the double bonds to form a conjugated diene; however, the addition of $.NO_2$ maintains a methylene-interrupted diene configuration to yield singly nitrated polyunsaturated fatty acids. This arrangement is similar to nitration products generated by the nitronium ion ($NO_2^+$), which can be produced by $ONOO^-$ reaction with heme proteins or via secondary products of $CO_2$ reaction with $ONOO^-$.

The reaction of polyunsaturated fatty acids with acidified nitrite ($HNO_2$) can generate a complex mixture of products similar to those formed by direct reaction with $.NO_2$, including the formation of singly nitrated products that maintain the bis-allylic bond arrangement. The acidification of $NO_2^-$ can create a labile species, $HNO_2$, which is in equilibrium with secondary products, including $N_2O_3$, .NO and $NO_2$, all of which can participate in nitration reactions. The relevance of this pathway as a mechanism of fatty acid nitration is exemplified by physiological and pathological conditions wherein $NO_2^-$ is exposed to low pH (e.g., <pH 4.0). This may conceivably occur in the gastric compartment, following endosomal or phagolysosomal acidification or in tissues following-post ischemic reperfusion.

Nitrated linoleic acid ($LNO_2$) has been shown to display robust cell signaling activities that are generally anti-inflammatory in nature. Synthetic $LNO_2$ can inhibit human platelet function via cAMP-dependent mechanisms and inhibits neutrophil $O_2^-$ generation, calcium influx, elastase release, CD11b expression and degranulation via non-cAMP, non-cGMP-dependent mechanisms. $LNO_2$ may also induce vessel relaxation in part via cGMP-dependent mechanisms. In aggregate, these data, derived from a synthetic fatty acid infer that nitro derivatives of fatty acids ($NO_2$-FA) represent a novel class of lipid-derived signaling mediators. To date, a gap in the clinical detection and structural characterization of nitrated fatty acids has limited defining $NO_2$-FA derivatives as biologically-relevant lipid signaling mediators that converge .NO and oxygenated lipid signaling pathways.

Embodiments of the invention are generally directed to activated fatty acids and, in particular, activated saturated or unsaturated fatty acids having at least one heteroatom interrupting the aliphatic chain of the fatty acid. As used herein an "activated fatty acid" refers to a fatty acid having at least one electron withdrawing group covalently bound to a carbon of the saturated or unsaturated aliphatic chain of a fatty acid. Such activated fatty acids may be substituted by any number of electron withdrawing groups at any number of positions on the hydrocarbon chain and such electron withdrawing groups may or may not be associated with a carbon-carbon double bond of an unsaturated fatty acid, a heteroatom, or a combination thereof. In various embodiments, at least one heteroatom of an activated fatty acid may be positioned adjacent to a carbon having an attached electron-withdrawing group, or at least one carbon-carbon double bond may be associated with an electron-withdrawing group. For example, in some embodiments, the activated fatty acids may include one or more heteroatoms on a saturated aliphatic chain, and an electron withdrawing group may be associated with a carbon adjacent to at least one of the one or more heteroatoms. In other embodiments, the activated fatty acid may include one or more heteroatoms and or one or more double bonds and an electron withdrawing group may be associated with either a carbon adjacent to at least one of the one or more heteroatoms, or at least one of the one or more double bonds, or both. Thus, in some embodiment, an activated fatty acid may have one electron-withdrawing group, and in other embodiments, an activated fatty acid may be substituted with multiple electron withdrawing groups at multiple positions along the hydrocarbon chain and adjacent to any combination of heteroatoms and/or double bonds.

In such embodiments, the electron-withdrawing group may be positioned on a carbon directly adjacent to a heteroatom to form an "electron withdrawing heteroatom" or a carbon directly attached to a double bond of the activated fatty acid forming an "electron withdrawing vinyl" group. The electron withdrawing group of such electron withdrawing heteroatoms or electron withdrawing vinyl groups may be on either side of the heteroatom or double bond such that the electron withdrawing group may be in either cis or trans configuration at a double bond or in either R or S absolute stereochemistry at an $sp^3$ chiral/stereogenic center.

In various embodiments, the heteroatom of an electron withdrawing heteroatoms may be any heteroatom known in the art. For example, the heteroatom of some embodiments may be an oxygen, a sulfur, or a nitrogen, and in particular embodiments, each heteroatom may be a sulfur or an oxygen. In still other embodiments, the heteroatom may be a sulfinyl (i.e., S=O). The heteroatom containing activated fatty acids encompassed by embodiments may have one or more heteroatoms at any position along the aliphatic hydrocarbon chain and as such, may have one or more electron withdrawing heteroatoms at any position along the aliphatic hydrocarbon chain. In other embodiments, heteroatom containing fatty acids, with 3, 4, 5, 6 or more heteroatoms, can have an electron withdrawing group on either carbon adjacent to any one heteroatom or a combination of heteroatoms or all of the heteroatoms. Thus, embodiments include all possible permutations of positions and electron-withdrawing groups available for each heteroatom containing fatty acid.

For example, in some exemplary embodiments, an activated 18 carbon fatty acid, may have a heteroatom replacing the $10^{th}$ (C-9) carbon, i.e., (E)-9-(pentylthio)dodecanoic acid or (E)-9-(pentyloxy)-dodecannoic acid, and an electron withdrawing group may be positioned at C-8 or C-10 or both. In other embodiments, an activated 18 carbon fatty acid may have heteroatoms replacing the $6^{th}$ (C-12) carbon and the $10^{th}$ (C-9) carbon, to provide, for example, 9-(2-(pentylthio)ethylthio)nonanoic acid, 9-(2-(pentyloxy)ethyloxy)nonanoic acid, 9-(2-(pentyloxy)ethylthio)nonanoic acid, 9-(2-(pentylthio)ethyloxy)nonanoic acid, and the like, and an electron withdrawing group may be positioned at any one or all of C-8, C-10, C-11, C-13, or combinations thereof. In yet other embodiments, an oleic acid may be couple to a thio or oxy carbonate, acetic acid, propionic acid, or butanoic acid derivatives of oleic acid. For example, embodiments include 3-(8-(octylthio)octylthio)propanoic acid, 3-(8-(octyloxy)octylthio)propanoic acid, 3-(8-(octylthio)octyloxy)propanoic acid, 3-(8-(octylthio)octylsulfinyl) propanoic acid and the like where a heteroatom replaces C-9 of an 18 carbon acid and an thiopropionic acid, oxypropionic acid, or sulfinylpropionic acid replaces the carboxy terminus. In such embodiments, an electron withdrawing group may be positioned at C-1, C-9, C-10, or the 2 position of the propionic acid or combinations thereof. Certain embodiments include 18 carbon fatty acids having two heteroatoms replacing, for example, C-9 and C-12 having at least one electron withdrawing group at C-8, C-10, C-11, C-13 or combinations there, and sill other embodiments, 20 or 22 carbon fatty acids having any number of heteroatoms replacing carbons on the aliphatic chains each having at least one electron withdrawing group positioned at a carbon adjacent to the heteroatom. In yet other embodiments, the heteroatom containing activated fatty acids described above may be cholesterol fatty acids.

In the case of electron withdrawing vinyl groups, fatty acids encompassed by embodiments may have one or more than one electron withdrawing vinyl groups at any carbon on the aliphatic hydrocarbon chain, and there are several ways that an unsaturated fatty acid can have one electron-withdrawing group. For example, in some exemplary embodiments, an activated oleic acid (octadec-12-enoic acid) which is an 18 carbon, ω-6 fatty acid with one double bond (denoted "18:1") between the $6^{th}$ (C-13) and $7^{th}$ (C-12) carbons, may have an electron withdrawing group at either C-13 or C-12. In other exemplary embodiments, an activated linoleic acid (octadeac-9,12,-dienoic acid), which is an 18 carbon, ω-6 fatty acid with two double bonds (denoted "18:2") between the $6^{th}$ (C-13) and $7^{th}$ (C-12) carbons and the 9th (C-10) and 10th (C-9) carbons, may have an electron withdrawing group at C-9 or C-10 or C-12 or C-13. In still other embodiments, an activated linoleic acid may have an electron withdrawing group at either C-9 or C-10 and C-12 or C-13, and in certain embodiments, an activated linoleic acid may have electron withdrawing groups at C-9 and C-10 and/or C-12 and C-13. In other embodiments, double bond containing fatty acids, with 3, 4, 5, 6 or more double bonds, can have an electron withdrawing group on either carbon of any one double bond or combination of double bonds or all of the double bonds. Thus, embodiments include all possible permutations of positions and electron-withdrawing groups available for each heteroatom containing fatty acid.

In analogy to the preceding descriptions of compounds with one electron-withdrawing group or two electron-withdrawing groups, it is also possible to have three, four, five or more electron withdrawing groups. Following the same logic in the preceding descriptions of compounds with one electron-withdrawing group or two electron-withdrawing groups, multiple heteroatom containing fatty acids, with 2, 3, 4, 5, 6, or more heteroatoms, and polyunsaturated fatty acids, with 3, 4, 5, 6 or more double bonds, can have multiple electron withdrawing (three, four, five or more, as available positions for substitution permit) at any of the positions on any of the carbons adjacent to heteroatoms or double bond carbons, including all possible permutations of positions and electron-withdrawing groups. Additionally, in any embodiments such as those described above, any number of non-electron-withdrawing groups may be covalently bound to carbons of the aliphatic chain of the activated fatty acid. For example, in some embodiments, the activated fatty acids of the invention may include one or more methyl, $C_2$-$C_6$ alkyl, alkenyl, or alkynyl or amino covalently attached to one or more carbons of the aliphatic chain of an activated fatty acid.

In particular embodiments, an activated fatty acid may have combinations of heteroatoms and double bonds. Thus, embodiments of the invention encompass activated fatty acids having one or more heteroatoms and one or more carbon-carbon doubles and one or more electron withdrawing groups at a carbon adjacent to a heteroatom or associated with a carbon of the carbon-carbon double bond or combinations thereof. For example, in some exemplary embodiments, an oleic acid may have a heteroatom at the 9th carbon (C-10) and a double bond at the 6th carbon (C-12), i.e., 9-(oct-2-enylthio)nonanoic acid or 9-(oct-2-enyloxy) nonanoic acid, or a heteroatom at the 6th carbon (C-12) and a double bond 9th carbon (C-10), i.e., 12-(pentylthio)dodec-9-enoic acid or 12-(pentyloxy)dodec-9-enoic acid and an electron with drawing group may be positioned on either carbon adjacent to the heteroatom and/or either carbon of the carbon-carbon double bond, both carbons adjacent to the heteroatom and/or both carbons of the carbon-carbon double bond, or any combination thereof. Similarly, in other embodiments, multiple heteroatom and double bond containing fatty acids, with 2, 3, 4, 5, 6, or more heteroatoms and 2, 3, 4, 5, 6 or more double bonds, can have multiple electron withdrawing (three, four, five or more, as available positions for substitution permit) at any of the positions on any of the carbons adjacent to heteroatoms or double bond carbons, including all possible permutations of positions and electron-withdrawing groups. In still other embodiments, an activated fatty acid may have one heteroatom and 2, 3, 4, 5, 6 or more double bonds, and in still further embodiments, an activated fatty acid may have one double bond and 2, 3, 4, 5, 6 or more heteroatoms, so long as at least one heteroatom is an electron withdrawing heteroatom or double bond at least one double bond is an electron withdrawing vinyl group.

In certain embodiments, a heteroatom of the activated fatty acid may be located at within, for example, the first 1, 2, 3, or 4 carbons from the carboxy terminus of the fatty acid to produce a carbonate, acetic acid, propionic acid, or butanoic acid derivatives of the activated fatty acid. For example, in some embodiments, a 18 carbon, or any length, aliphatic hydrocarbon chain may be associated with a mercaptoacetic acid or hydroxyacetic acid to produce an octadecylthioacetic acid or an octadecyloxyacetic acid, and an electron withdrawing group may be associated with one or both of the carbons adjacent to the heteroatom. In other embodiments, the aliphatic hydrocarbon chain may include one or more double bond, and in certain embodiments, at least one of these double bonds may include an electron withdrawing group associated with one or both carbons of the double bonds to produce an electron withdrawing vinyl group. In still other embodiments, the aliphatic carbon chain may include one or more additional heteroatoms, and in some embodiments, at least one of the additional heteroatoms may be an electron withdrawing heteroatom. In yet other embodiments, the aliphatic chain may include one or more double bonds and one or more additional heteroatoms and, in some embodiments, any one or any combination of the double bonds or additional heteroatoms may be an electron withdrawing vinyl group or an electron withdrawing heteroatom.

In particular embodiments, the heteroatom associated with the carbonate, acetic acid, propionic acid, or butanoic acid may not include an associated electron withdrawing group, and therefore the aliphatic hydrocarbon chain associated with the thio- or oxy-carbonate, acetic acid, propionic acid, or butanoic acid should include at least one electron withdrawing vinyl group or at least one electron withdrawing heteroatom. For example, in some embodiments, an octadecylthioacetic acid or an octadecyloxyacetic acid may have one or more double bond included within the 18 carbon aliphatic hydrocarbon chain and at least one of these double bonds may be an electron withdrawing vinyl group. In other embodiments, an octadecylthioacetic acid or an octadecyloxyacetic acid may have one or more additional heteroatoms included within the 18 carbon aliphatic hydrocarbon chain and at least one of these additional heteroatoms may be an electron withdrawing heteroatom. In still other embodiments, an octadecylthioacetic acid or an octadecyloxyacetic acid may have one or more double bond and one or more additional heteroatom included within the 18 carbon aliphatic hydrocarbon chain and at least one of these double bonds or heteroatoms may be an electron withdrawing vinyl group or an electron withdrawing heteroatom. As indicated above, numerous permutations of such compounds encompassing various combinations of double bonds, heteroatoms, electron withdrawing vinyl groups, electron withdrawing heteroatoms associated with aliphatic chains of various lengths can be envisioned based on these exemplary embodiments and are encompassed by the invention.

For example, in some exemplary embodiments, an activated 18 carbon fatty acid, i.e., oleic acid, may have a heteroatom replacing the 6th carbon (C-12) on the aliphatic hydrocarbon chain and a double bond at the 10th (C-9) carbon, i.e., (E)-12-(pentylthio)dodec-9-enoic acid or (E)-12-(pentyloxy)-dodec-9-enoic acid, and an electron withdrawing group positioned at C-7, C-8, C-9, C-10, C-11 or C-13 or combinations thereof. In other embodiments, an oleic acid may have heteroatoms replacing the 6th (C-12)

carbon and the carbon 1, 2, 3, or 4 and a double bond at the 10th (C-9) carbon, to provide, for example, (E)-3-(8-(pentylthio)oct-5-enylthio)propanoic acid, (E)-3-(8-(pentyloxy) oct-5-enyloxy)propanoic acid, (E)-3-(8-(pentylthio)oct-5-enyloxy)propanoic acid, (E)-3-(8-(pentyloxy)oct-5-enylthio)propanoic acid and the like, and an electron withdrawing group may be positioned at any one or all of C-8, C-10, C-11, C-7, C-13, C-1, or C-2. In yet other embodiments, an oleic acid may be couple to a thio or oxy carbonate, acetic acid, propionic acid, or butanoic acid derivatives of oleic acid. For example, embodiments include (E)-2-(11-(pentylthio)undec-8-enylthio)acetic acid and (E)-2-(11-(pentyloxy)undec-8-enylthio)acetic acid where a heteroatom replaces C-12 of an oleic acid with a carbon-carbon double bond at C-9 and an thioacetic acid replaces the carboxy terminus. In such embodiments, an electron withdrawing group may be positioned at C-7, C-8, C-9, C-10, C-11 or C-13 or combinations thereof. In certain embodiments, any of the oleic acids described above having at least one heteroatom may be cholesterol oleic acids.

Still other embodiments include linoleic acid derivatives having at least one heteroatom or gamma linoleic acid derivatives having at least one heteroatom, and the heteroatoms and electron withdrawing groups may be arranged as described for oleic acid. For example, embodiments include (9E,12E)-14-(propylthio)tetradeca-9,12-dienoic acid, (9E, 12E)-14-(propyloxy)tetradeca-9,12-dienoic acid, 6-((2E, 5E)-undeca-2,5-dienylthio)hexanoic acid, (E)-10-((E)-hept-1-enylthio)dec-9-enoic acid, (E)-10-((E)-hept-1-enyloxy) dec-9-enoic acid, 6-((2E,5E)-undeca-2,5-dienyloxy) hexanoic acid, and 6-((2E,5E)-7-(propylthio)hepta-2,5-dienylthio)hexanoic acid each having electron withdrawing groups at at least one carbon of a carbon-carbon double bond or the carbon adjacent to the carbon of a carbon-carbon double bond or a carbon adjacent to a heteroatom, and combinations thereof. Other exemplary embodiments include gamma linoleic acids (6E,9E,12E)-14-(propylthio) tetradeca-6,9,12-trienoic acid, (6E,9E,12E)-14-(propyloxy) tetradeca-6,9,12-trienoic acid, (6E ,9E)-10-((E)-hept-1-enylthio)deca-6,9-dienoic acid, (6E,9E)-10-((E)-hept-1-enyloxy)deca-6,9-dienoic acid, 2-((3E,6E,9E)-pentadeca-3, 6,9-trienylthio)acetic acid, 2-((3E,6E,9E)-pentadeca-3,6,9-trienyloxy)acetic acid, 2-((3E,6E,9E)-11-(propylthio) undeca-3,6,9-trienylthio)acetic acid, 2-((3E,6E,9E)-11-(propyloxy)undeca-3,6,9-trienyloxy)acetic acid, 2-((3E,6E, 9E)-11-(propyloxy)undeca-3,6,9-trienylthio)acetic acid and the like each having electron withdrawing groups at at least one carbon of a carbon-carbon double bond or the carbon adjacent to the carbon of a carbon-carbon double bond or a carbon adjacent to a heteroatom, and combinations thereof. In yet other embodiments, linoleic acid and gamma linoleic acids may have a heteroatom that was introduced by coupling linoleic acid or gamma linoleic acids to a thio or oxy carbonate, acetic acid, propionic acid, or butanoic acid. For example, embodiments, include 3-((8E,11E)-13-(propylthio)trideca-8,11-dienylthio)propanoic acid, 3-((8E,11E)-13-(propyloxy)trideca-8,11-dienylthio)propanoic acid, 3-((5E,8E,11E)-13-(propylthio)trideca-5,8,11-trienylthio) propanoic acid, 3-((5E,8E,11E)-13-(propyloxy)trideca-5,8, 11-trienylthio)propanoic acid, 3-((5E,8E,11E)-13-(propylthio)trideca-5,8,11-trienylsulfinyl)propanoic acid, 3-((5E, 8E,11E)-13-(propyloxy)trideca-5,8,11-trienylsulfinyl) propanoic acid, and the like each having electron withdrawing groups at at least one carbon of a carbon-carbon double bond or the carbon adjacent to the carbon of a carbon-carbon double bond or a carbon adjacent to a heteroatom, and combinations thereof. In certain embodiments, any of the linoleic acids and gamma linoleic acids described above having at least one heteroatom may be cholesterol oleic acids.

Further embodiments, include arachidonic acids, eicosapentaenoic acid, and docosahexanoic acids having at least one heteroatom replacing a carbon of the aliphatic chain, and still further embodiments, include arachidonic acids, eicosapentaenoic acid, and docosahexanoic acids that have been coupled to a thio or oxy carbonate, acetic acid, propionic acid, or butanoic acid to introduce a heteroatom. In each such embodiment, one or more electron withdrawing groups may be positioned at at least one carbon of a carbon-carbon double bond or the carbon adjacent to the carbon of a carbon-carbon double bond or a carbon adjacent to a heteroatom, and combinations thereof.

While the exemplary compounds described above show double bonds in the E conformation, embodiments of the invention encompass activated fatty acids having double bonds in the Z conformation or in any combination of E and Z conformations.

The term "electron-withdrawing group" is recognized in the art and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant (see, e.g., J. March, Advanced Organic Chemistry, McGraw Hill Book Company, New York, (1977 edition) pp. 251-259). The Hammett constant values are generally negative for electron donating groups and positive for electron withdrawing groups. For example the Hammet constant for para substituted $NH_2$ ($\sigma[P]$) is about $-0.7$ and the $\sigma[P]$ for a nitro group is about 0.8.

Embodiments of the invention encompass any known electron withdrawing group. For example, electron-withdrawing groups may include, but are not limited to, aldehyde (—COH) acyl (—COR), carbonyl (—CO), carboxylic acid (—COOH), ester (—COOR), halides (—Cl, —F, —Br, etc.), fluoromethyl (—$CF_n$), cyano (—CN), sulfonyl (—$SO_n$), sulfone (—$SO_2R$), sulfonic acid (—$SO_3H$), 1°, 2° and 3° ammonium (—$NR_3^+$), and nitro(—$NO_2$) where each R may, independently, be hydrogen, methyl, or $C_2$ to $C_6$ alkyl, alkenyl, or alkynyl. In some embodiments, the electron withdrawing group may be a strong electron withdrawing group having a $\sigma$ of at least about 0.2, and in certain embodiments, the electron withdrawing group may form a dipole. For example, in particular embodiments, the electron withdrawing group may be a nitro, ammonium or sulfonyl. In other embodiments, the activated fatty acids of the invention may be additionally substituted by non-electron withdrawing groups or electron donating groups including, for example, alcohol (—OH), reverse ester (—OOCR), alkyl, alkenyl, alkynyl, 1° and 2° amines (—$NR_2$), nitrate (—$ONO_2$), nitrito (—ONO) and the like.

The fatty acids of embodiments may be any unsaturated and polyunsaturated fatty acid known in the art. The term "fatty acid" describes aliphatic monocarboxylic acids. Various embodiments include activated fatty acids having an aliphatic hydrocarbon chain identical or similar to identified, naturally occurring fatty acids. For example, aliphatic hydrocarbon chains of known naturally occurring fatty acids are generally unbranched and contain an even number of from about 4 to about 24 carbons, and others include fatty acids having from 12 to 18 carbons in the aliphatic hydrocarbon chain. In still other embodiments, fatty acids may have greater than 24 carbons in the aliphatic hydrocarbon chain. Embodiments of the invention encompass such naturally occurring fatty acids as well as naturally or non-naturally occurring fatty acids, which may contain an odd number of carbons and/or a naturally or non-naturally occurring linker. Thus, some embodiments of the invention include fatty acids having an odd number of carbons of, for example, from 5 to 23 carbons, and in other embodiments, from 11 to 17 carbons. In yet other embodiments, the fatty acids of embodiments may have greater than 23 carbons. The naturally and naturally or non-naturally occurring fatty acids of the invention may also be branched at one or more location along the hydrocarbon chain, and in various embodiments, each branch may include an aliphatic hydrocarbon chain of from 1 to 24 carbons, 2 to 20 carbons or 4 to 18 carbons wherein each branch may have an even or odd number of carbons.

The aliphatic hydrocarbon chain of fatty acids of various embodiments may be unsaturated or polyunsaturated. The term "unsaturated" refers to a fatty acid having a aliphatic hydrocarbon chain that includes at least one double bond and/or substituent. In contrast, a "saturated" hydrocarbon chain does not include any double bonds or substituents. Thus, each carbon of the hydrocarbon chain is 'saturated' and has the maximum number of hydrogens. "Polyunsaturated," generally, refers to fatty acids having hydrocarbon chains with more than one double bond. The double bonds of the unsaturated or polyunsaturated fatty acids of various embodiments may be at any location along the aliphatic hydrocarbon chain and may be in either cis or trans configuration. The term "cis," refers to a double bond in which carbons adjacent to the double bond are on the same side and the term "trans" refers to a double bond in which carbons adjacent to the double bond are on opposite sides. Typically "cis" is the same as Z, and "trans" is the same as E but sometimes the IUPAC rules for naming compounds will give the opposite of this, which is the typical case in nitroalkenes. For example, a nitroalkene can have the two carbon groups "cis" but the two groups that take priority for the naming of compounds (a nitro group on one carbon of the alkene and a carbon group on the other carbon of the alkene) are on opposite sides and thus are E. Therefore the nitroalkene analog of a "cis" double bond is actually an E nitroalkene. Similarly, the nitroalkene analog of a "trans" double bond is actually a Z nitroalkene. Without wishing to be bound by theory, double bonds in cis configuration along the carbon chain (cis carbon chain but E nitroalkene) may induce a bend in the hydrocarbon chain. Double bonds in "trans," configuration along the carbon chain (trans carbon chain but Z nitroalkene) may not cause the hydrocarbon chain to bend. Embodiments of the invention may include activated fatty acids having double bonds in either cis or trans configuration, and encompass compositions that may include combinations of cis and trans containing activated fatty acids and regioisomers of the activated fatty acids.

Many unsaturated and polyunsaturated fatty acids have been identified and are known to be naturally occurring. Such unsaturated or polyunsaturated naturally occurring fatty acids, generally, include an even number of carbons in their aliphatic hydrocarbon chain. For example, a naturally occurring unsaturated or polyunsaturated fatty acid may have, 4, 6, 8, 10, 12, 14, 16, 18, 20, 22 and so on carbons and may include omega ($\omega$)-3, $\omega$-5, $\omega$-6, $\omega$-7, $\omega$-9 fatty acids and the like. Any such fatty acid may be useful in embodiments of the invention. The symbol '$\omega$' is used to refer to the terminal methyl carbon of the aliphatic hydrocarbon chain. The placement of the double bond of the $\omega$-X fatty acid is the carbon-carbon bond X number of carbons from the $\omega$ carbon. For example, an $\omega$-6 fatty acid has a double bond between the $6^{th}$ and $7^{th}$ carbons counting backward from the $\omega$ carbon and an $\omega$-3 fatty acid has a double bond between the $3^{rd}$ and $4^{th}$ carbons counting backward from the $\omega$ carbon. Various embodiments of the invention include nitrated $\omega$-3 fatty acids, including, but not limited to, linolenic acid, alpha-linolenic acid, eicosapentanoic acid, docosapentaenoic acid, docosahexanoic acid and stearidonic acid; nitrated $\omega$-5 fatty acids including, but not limited to, myristoleic acid; nitrated $\omega$-6 fatty acids including, but not limited to, linoleic acid, gamma-linoleic acid, dihomo-gamma-linoleic acid and arachidonic acid; nitrated $\omega$-7 fatty acids including, but not limited to, palmitoleic acid; and nitrated $\omega$-9 fatty acids including, but not limited to, oleic acid and erucic acid. Of course, the fatty acids of the invention may also be referred to using IUPAC nomenclature in which the placement of the double bond is determined by counting from the carbon of the carboxylic acid, and 'C—X' denotes the carbon in aliphatic hydrocarbons using IUPAC nomenclature wherein X is the number of the carbon counting from the carboxylic acid. Embodiments of the invention also include synthetic equivalents to naturally occurring fatty acids and derivatives thereof.

In some embodiments, the naturally occurring fatty acids described above may be modified to include a heteroatom. For example, a naturally occurring 4, 6, 8, 10, 12, 14, 16, 18, 20, 22 and so on carbon fatty acid or $\omega$-3, $\omega$-5, $\omega$-6, $\omega$-7, $\omega$-9 fatty acids and the like, may be coupled to a thio- or oxy-carbonate, acetic acid, propionic acid, or butanoic acid. Techniques for preparing such modified fatty acids are known in the art, and any such method may be used.

Other embodiments of the invention include unsaturated or polyunsaturated naturally or non-naturally occurring fatty acids which may have an odd number of carbons such as, for example, 5, 7, 9, 11, 13, 15, 17, 19, 20, 21 and so on. As in naturally occurring fatty acids, the one or more double bonds associated with naturally or non-naturally occurring fatty acids may be at any position along the aliphatic hydrocarbon chain, and the double bonds may be in either cis or trans configuration. In yet other embodiments, the naturally or non-naturally occurring fatty acids may include one or more linker groups, which interrupt the aliphatic hydrocarbon chain. For example, in some embodiments, activated fatty acids may have one or more non-carbon-carbon linkage such as, for example, ester, ether, vinyl ether, amino, imine and the like at any position within the aliphatic hydrocarbon chain. Similarly, in other embodiments, activated polyunsaturated naturally or non-naturally occurring fatty acids may have one or more heteroatoms at any position within the aliphatic hydrocarbon chain.

Various embodiments of the invention include unsaturated or polyunsaturated fatty acids that may have a carbon-carbon double bond between any two carbons of the aliphatic chain of the fatty acid, and any number of carbon-carbon double bonds may be present in such polyunsaturated fatty acids. For example in some embodiments, polyunsaturated fatty acids may have 2, 3, 4, 5, 6 or more carbon-carbon double bonds. In such embodiments, each of the more than one carbon-carbon double bond may individually be in either cis or trans configuration. In some embodiments, at least one of the carbon-carbon double bonds of a polyunsaturated fatty acid may have an associated electron withdrawing group, and in other embodiments, more than one of the carbon-carbon double bonds of such polyunsaturated fatty acids may have an associated electron withdrawing group. Additionally, in such embodiments, the electron withdrawing group may be associated with either carbon of the carbon-carbon double bond or a carbon directly adjacent to either carbon of the carbon-carbon double bond. For example, in some embodiments, an electron withdrawing group may be attached to the alpha (α) carbon of the carbon-carbon double bond, and in other embodiments, an electron withdrawing group may be associated with the beta (β) carbon of the carbon-carbon double bond. In still other embodiments, an electron withdrawing group may be associated with the gamma (γ) carbon, the carbon directly adjacent to, and attached to, a carbon-carbon double bond. In embodiments where a polyunsaturated fatty acid includes two or more carbon-carbon double bonds along the aliphatic chain and an electron withdrawing group is associated with any of the two or more carbon-carbon double bonds or each of the two or more of the carbon-carbon double bonds, each electron withdrawing group may be attached to any carbon associated with each individual carbon-carbon double bonds. For example, in some embodiments, an electron withdrawing group may be associated with each of the double bonds, with the electron group attached to either the (α) carbon, the beta (β) carbon or the gamma (γ) carbon of each double bond. In other embodiments, some of the double bonds can have an attached electron withdrawing group and some of the double bonds will not have attached electron withdrawing groups, and those double bonds that do have attached electron withdrawing groups can have electron withdrawing groups attached at either the (α) carbon, the beta (β) carbon or the gamma (γ) carbon of each double bond. Similarly, in embodiments in which the activated fatty acid includes a heteroatom, an electron withdrawing group may be attached to either of the adjacent carbon atoms, or within at least one carbon of the carbon immediately adjacent to the heteroatom.

In particular embodiments, an unsaturated fatty acid having at least one electron withdrawing group may be a conjugated fatty acid. In such embodiments, two carbon-carbon double bonds in an aliphatic chain are adjacent to one another such that there is no methylene group between them. Such conjugated compounds are commonly called 1,3-dienes, or conjugated fatty acids. Such 1,3-dienes may include one or more electron withdrawing groups at any of 6 positions, at the 1, 2, 3, and/or 4 positions of the 1,3-dienes and at the two carbons adjacent to the diene (at the 0 and 5 positions, in relation to the 1, 2, 3, 4 method of identifying carbons in a 1,3-diene). For example, one associated electron withdrawing group may be attached to any of the 6 positions identified above, that is to either the 1, 2, 3, or 4 positions on the diene or to either of the carbons adjacent to the 1,3-diene (at the 0 or 5 positions, as described above). In additional embodiments, two associated electron withdrawing groups could be attached to any two of the six possible positions, three associated electron withdrawing groups could be attached to any two of the six possible positions, four associated electron withdrawing groups could be attached to any two of the six possible positions, five associated electron withdrawing groups could be attached to any two of the six possible positions, and six associated electron withdrawing groups could be attached to any two of the six possible positions. In summary, any configuration of electron withdrawing groups attached to any of the six positions described above in a 1,3-diene are encompassed by embodiments of the invention.

In certain embodiments, the activated fatty acids of the invention may undergo an isomerization following preparation such that either the cis/trans configuration of the double bond, the location of the double bond in the carbon chain, or both, may change. For example, in some embodiments, a activated fatty acid may be prepared with a carbon-carbon double bond of having an electron withdrawing group attached to a gamma carbon of a carbon-carbon double bond. Following preparation, the carbon-carbon double bond may undergo an isomerization such that the electron withdrawing group is now conjugated with the carbon-carbon double bond after isomerization. Such isomerizations may occur spontaneously at any time following preparation, and may result in a composition which may have initially been prepared as including a single species of activated fatty acid that subsequently includes a combination of isomers of the first-prepared activated fatty acid originally produced. In other embodiments, an activated fatty acid may be prepared having an electron withdrawing group attached to a gamma carbon of a carbon-carbon double bond, and this carbon-carbon double bond may undergo an isomerization following administration such that an activated fatty acid is produced having the electron withdrawing group is conjugated with the carbon-carbon double bond.

In still other embodiments, the carboxy-terminal end of the activated fatty acid may be modified. For example, in some embodiments, the fatty acid may include a glycerol associated with the carboxy-terminal end of the fatty acid to create a glycerolipid, and such glycerolipids may be mono-, di-, or tri-glycerides wherein at least one of the fatty acids of a di- or tri-glyceride may be an activated fatty acid and any remaining fatty acids may be a saturated or unsaturated fatty acid. Similarly, in other embodiments, a carbohydrate may be associated with the carboxy-terminal end of an activated fatty acid to form a glycolipid. In such embodiments, any carbohydrate known in the art may be a carbohydrate moiety of a glycolipid including, but not limited to, galactose and glucose. In yet other embodiments, a carbohydrate may be associated with a glyceride which is associated with the carboxy-terminal end of an activated fatty acid to form a glycero-glycolipid, which may have one or two activated fatty acids associated with the glycero-portion of the glycero-glycolipid and, in embodiments in which only one activated fatty acid is associated with the glycero-glycolipid, the remaining position on the glycerol may include a saturated or unsaturated fatty acid or hydrogen, alkyl, or a functional group such as, for example, alcohol, amine, phosphate, phosphonic acid, thiol, sulfonic acid and the like. In certain embodiments, the carboxy-terminal end of the activated fatty acids of the invention may be associated with a phosphate to from a phospholipid. In such embodiments, the phosphate may be directly associated with the fatty acid through the carboxy-terminus, or the phosphate may be associated with a di-glyceride wherein one or two activated fatty acids are attached glycerol moiety and, in embodiments where only one activated the fatty acid is attached to the glycerol, remaining position on the glycerol may include a saturated or unsaturated fatty acid or hydrogen, alkyl, or a functional group such as, for example, alcohol, amine, phosphate, phosphonic acid, thiol, sulfonic acid and the like. In further embodiments, the carboxy-terminus of the activated fatty acid may be associated with a cholesterol or other sterol moiety. In yet other embodiments, the carboxy-terminal end may be modified by the covalent attachment of a secondary active agent. In the particular embodiments, carboxy-terminal modifications including a glycerol may not include a nitro group. Without wishing to be bound by theory, modification of the carboxy-terminal end of activated fatty acids may enhance partitioning of the activated fatty acid after administration and may also improve resilience of the activated fatty acid by inhibiting beta-oxidation in mitochondria following administration.

For example, embodiments of the invention include compounds of general formulae I, II, and III:

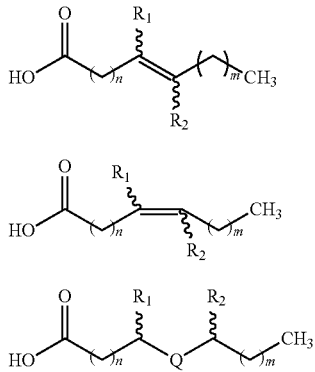

wherein $R_1$ and $R_2$ are independently selected from —H and any electron withdrawing groups including, but not limited to —COH, —COR, —CO, —COOH, —COOR, —Cl, —F, —Br, —I, —CF$_3$, —CN, —SO$_3^-$, —SO$_2$R, —SO$_3$H, —NH$_3^+$, —NH$_2$R$^+$, —NHR$_2^+$, —NR$_3^+$ and —NO$_2^-$ wherein at least one of $R_1$ and $R_2$ is an electron withdrawing group, Q is a heteroatom, and m and n are, independently, 1-20. Some embodiments include compounds of general formulae IV, V, and VI:

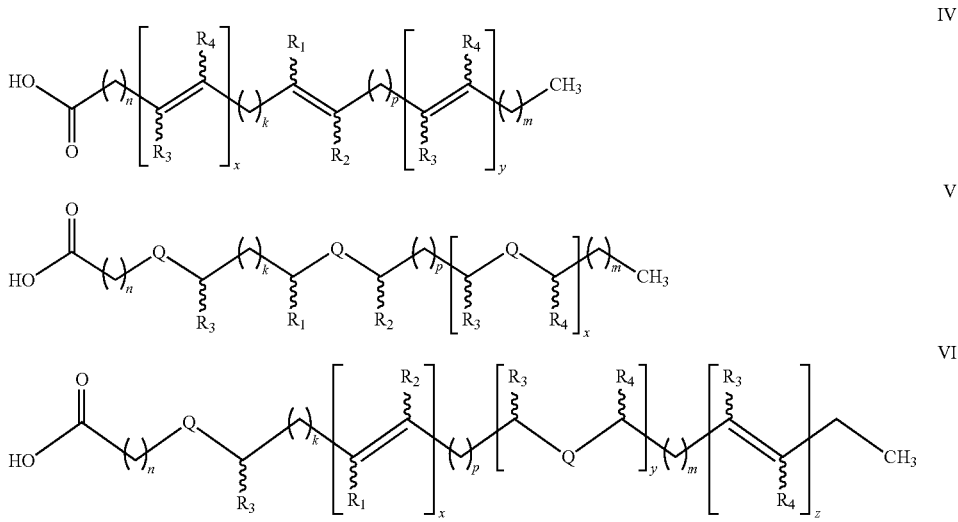

wherein $R_1$, $R_2$, m and n are as described above, $R_3$ and $R_4$ are, independently, selected from —H, —COH, —COR, —CO, —COOH, —COOR, —Cl, —F, —Br, —I, —CF$_3$, —CN, —SO$_3^-$, —SO$_2$R, —SO$_3$H, —NH$_3^+$, —NH$_2$R$^+$, —NHR$_2^+$, —NR$_3^+$ and —NO$_2^-$, k and p are, independently, 0 to 5 and x, y, and z are independently, 0 to 3, and wherein each double bond is in either cis or trans configuration. In still other embodiments, any carbon associated with m, n, k or p may be substituted.

Compounds encompassed by the formulae described above include, but are not limited to, (E)-9-nitro-octadec-9-enoic acid, (E)-10-nitro-octadec-9-enoic acid, (E)-8-nitro-octadec-9-enoic acid, (E)-11-nitro-octadec-9-enoic acid, (E)-10-acetyloctadec-9-enoic acid, (E)-9-aceto-octadec-9-enoic acid, (E)-11-aceto-octadec-9-enoic acid, (E)-8-aceto-octadec-9-enoic acid, (E)-10-chloro-octadec-9-enoic acid, (E)-9-chloro-octadec-9-enoic acid, (E)-11-chloro-octadec-9-enoic acid, (E)-8-chloro-octadec-9-enoic acid, (E)-10-sulfonyloctadec-9-enoic acid, (E)-9-sulfonyloctadec-9-enoic acid, (E)-11-sulfonyloctadec-9-enoic acid, and (E)-8-sulfonyloctadec-9-enoic acid, and salts thereof. Other embodiments include the Z-isomer or combinations of Z- and E-isomers of such compounds.

In other embodiments, the compounds of the invention may include, but are not limited to 2-((all-E)-9-nitrooctadeca-6,9,12-trienyloxy)acetic acid, 2-((all-E)-10-nitrooctadeca-6,9,12-trienyloxy)acetic acid, 2-((all-E)-8-nitrooctadeca-6,9,12-trienyloxy)acetic acid, 2-((all-E)-11-nitrooctadeca-6,9,12-trienyloxy)acetic acid, 2-((all-E)-9-nitrooctadeca-9,12,15-trienyloxy)acetic acid, 2-((all-E)-10-nitrooctadeca-6,9,12-trienyloxy)acetic acid, 2-((all-E)-8-nitrooctadeca-6,9,12-trienyloxy)acetic acid, 2-((all-E)-11-nitrooctadeca-6,9,12-trienyloxy)acetic acid, 2-(all-E)-(8-nitroeicosa-5,8,11,14-tetraenylthio)acetic acid, 2-(all-E)-(9-nitroeicosa-5,8,11,14-tetraenylthio)acetic acid, 2-(all-E)-(7-nitroeicosa-5,8,11,14-tetraenylthio)acetic acid, 2-(all-E)-(10-nitroeicosa-5,8,11,14-tetraenylthio)acetic acid, 3-(all-E)-(8-nitroeicosa-5,8,11,14-tetraenylthio)propionic acid, 3-(all-E)-(9-nitroeicosa-5,8,11,14-tetraenylthio)propionic acid, 3-(all-E)-(7-nitroeicosa-5,8,11,14-tetraenylthio)propionic acid, 3-(all-E)-(10-nitroeicosa-5,8,11,14-tetraenylthio) propionic acid, 3-(3E,6E)-6-nitronona-3,6-dienylthiopropionic acid, 3-(3E,6E)-7-nitronona-3,6-dienylthiopropionic acid, 3-(1-nitrotetradecylthio)propanoic acid, 3-nitro-3-(tetradecylthio)propanoic acid, 2-(1-nitrotetradecylthio)propanoic acid, 2-nitro-3-(tetradecylthio)propanoic acid, 3-(all-E)-(9,12-dinitrooctadeca-9,12,15-trienthio)propionic acid, 3-(all-E)-(9,15-dinitrooctadeca-9,12,15-trienthio)propionic acid, 3-(all-E)-(12,15-dinitrooctadeca-9,12,15-trienthio) propionic acid, 3-(all-E)-(9,12,15-trinitrooctadeca-9,12,15-trienthio)propionic acid, 3-(1-nitrotetradecylsulfinyl)propionic acid, 3-nitro-3-tetradecylsulfinyl)propionic acid, 3-nitro-3-(1-nitrotetradecylsulfinyl)propionic acid, 2-(1-nitrotetradecylsulfinyl)acetic acid, 2-nitro-2-(tetradecylsulfinyl)acetic acid, 2-((9E,12E)-9-nitrooctadeca-9,12-dienylsulfinyl)acetic acid, 2-((9E,12E)-8-nitrooctadeca-9,12-dienylsulfinyl)acetic acid, and 2-((9E,12E)-12- nitrooctadeca-9,12-dienylsulfinyl)acetic acid and salts thereof. Still other embodiments include the Z-isomer or combinations of Z- and E-isomers of such compounds.

The activated fatty acids described above may be prepared as a pharmaceutically acceptable formulation. The term "pharmaceutically acceptable" is used herein to mean that the compound is appropriate for use in a pharmaceutical product. For example, pharmaceutically acceptable cations include metallic ions and organic ions. More preferred metallic ions include, but are not limited to, appropriate alkali metal salts, alkaline earth metal salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include, without limitation, hydrochloric acid, hydroiodic acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

Isomeric and tautomeric forms of activated fatty acids of the invention as well as pharmaceutically acceptable salts of these compounds are also encompassed by the invention. Exemplary pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, .beta.-hydroxybutyric, galactaric and galacturonic acids.

Suitable pharmaceutically acceptable base addition salts used in connection with the activated fatty acids of the invention include metallic ion salts and organic ion salts. Exemplary metallic ion salts include, but are not limited to, appropriate alkali metal (group Ia) salts, alkaline earth metal (group IIa) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention.

Activated fatty acids as described in various embodiments of the invention above, may be administered to individuals to treat, ameliorate and/or prevent a number both acute and chronic inflammatory and metabolic conditions. In particular embodiments, activated fatty acids may be used to treat acute conditions including general inflammation, autoimmune disease, autoinflammatory disease, arterial stenosis, organ transplant rejection and burns, and chronic conditions such as, chronic lung injury and respiratory distress, diabetes, hypertension, obesity, arthritis, neurodegenerative disorders and various skin disorders. However, in other embodiments, activated fatty acids may be used to treat any condition having symptoms including chronic or acute inflammation, such as, for example, arthritis, lupus, Lyme's disease, gout, sepsis, hyperthermia, ulcers, enterocolitis, osteoporosis, viral or bacterial infections, cytomegalovirus, periodontal disease, glomerulonephritis, sarcoidosis, lung disease, lung inflammation, fibrosis of the lung, asthma, acquired respiratory distress syndrome, tobacco induced lung disease, granuloma formation, fibrosis of the liver, graft vs. host disease, postsurgical inflammation, coronary and peripheral vessel restenosis following angioplasty, stent placement or bypass graft, coronary artery bypass graft (CABG), acute and chronic leukemia, B lymphocyte leukemia, neoplastic diseases, arteriosclerosis, atherosclerosis, myocardial inflammation, psoriasis, immunodeficiency, disseminated intravascular coagulation, systemic sclerosis, amyotrophic lateral sclerosis, multiple sclerosis, Parkinson's disease, Alzheimer's disease, encephalomyelitis, edema, inflammatory bowel disease, hyper IgE syndrome, cancer metastasis or growth, adoptive immune therapy, reperfusion syndrome, radiation burns, alopecia and the like.

When administered, activated fatty acids may interact with a number of cellular receptors and/or proteins that mediate inflammation, either by inhibiting or stimulating their activity thereby inhibiting or reducing inflammation. Without wishing to be bound by theory, activated fatty acids may modulate important signaling activities including, for example, neurotransmission, gene expression, vascular function and inflammatory responses, and chemical properties of activated fatty acids that may facilitate these activities include, but are not limited to, the strong, reversible electrophilic nature of the β carbon adjacent to the electron withdrawing vinyl group, an ability to undergo Nef-like acid base reactions to release NO, an ability to partition into both hydrophobic and hydrophilic compartments, and a strong affinity for G-protein coupled receptors and nuclear receptors.

For example, in one embodiment, activated fatty acids may be administered to mediate cell signaling via multiple G-protein coupled receptors and nuclear receptors such as, but not limited to, peroxisome proliferator-activated receptors (PPAR) including PPARα, PPARγ, and PPARδ. PPAR is a nuclear receptor that is expressed throughout an organism, including in monocytes/macrophages, neutrophils, endothelial cells, adipocytes, epithelial cells, hepatocytes, mesangial cells, vascular smooth muscle cells, neuronal cells and when "activated" induces transcription of a number of target genes. Activation of PPAR has been shown to play various roles in regulating tissue homeostasis including, for example, increasing insulin sensitivity, suppress chronic inflammatory processes, reduce circulating free fatty acid levels, correct endothelial dysfunction, reduce fatty streak formation, delay plaque formation, limit blood vessel wall thickening and enhance plaque stabilization and regression. The activated fatty acids embodied herein may perform each of these functions associated with PPAR activation.

Moreover, activated fatty acids may perform these functions without significantly altering normal cellular process. For example, in one embodiment, an activated fatty acid may be administered to treat hypertension by lowering blood pressure to normal levels without reducing the blood pressure of the individual below normal levels even if the activated fatty acid is over-administered. Thus, without wishing to be bound by theory, the activated fatty acids of the invention may provide treatment of an individual without the negative affects associated with over-administration or over-treatment using traditional medications.

Activation of PPAR has been shown to be induced either directly or in part by a locking reaction in which a critical thiol in a highly conserved cysteine (Cys 285 of human PPARγ) which is located in a ligand binding domain of PPAR. Partial activation of PPAR has been shown to occur when relatively high concentrations of known thiol reactive compounds, such as 15-deoxy-$\Delta^{12,14}$-prostaglandin $J_2$ (15-d $PGJ_2$), are administered. Without wishing to be bound by theory, activated fatty acids may bind to PPAR covalently at the reactive thiol in the ligand binding domain of PPAR. Moreover, activated fatty acids may induce a conformational change in PPAR. More specifically, activated fatty acid binding may result in the C-terminus of the ligand binding domain (α-helix 12) to adopt an active conformation that may promote a beneficial pattern of co-repressor release and co-activator recruitment. Thus, activated fatty acids may enhance PPAR activation and transcription of PPAR regulated genes beyond that of known PPAR activating compounds.

In addition to activation of PPAR, activated fatty acid administration may be useful for activating a number of other factors important for cell signaling. For example, in one embodiment, activated fatty acids may be administered to induce gene expression and tissue activity of heme oxygenase-1 (HO-1) which has been shown to mediate adaptive and protective responses during inflammation, and activation of an adaptive or protective inflammatory response mediated by HO may be useful in treating inflammatory diseases such as, but not limited to, atheroscelrosis, acute renal failure, vascular restinosis, transplant rejection, and sepsis. In another embodiment, activated fatty acids may induce a reversible post-translational modification of proteins, such as, for example, glutathione (GSH) and glyceraldehyde-3-phosphate dehydrogenase (GAPDH) by covalently binding to catalytic cysteines on such proteins. Without wishing to be bound by theory, the covelent modification of these proteins by activated fatty acids may increase the hydrophobicity of these proteins inducing translocation of to membranes and suggests a role for redox regulation of enzyme function, cell signaling and protein trafficking. In yet another embodiment, activated fatty acids may be administered to repress NF-κB dependent gene expression and endothelial tumor necrosis factor-α induced expression of vascular cell adhesion molecules in monocytes and macrophages which results in inhibition of rolling and adhesion during inflammation. Thus, activated fatty acids may be useful for treating general inflammation resulting from surgery, injury or infection. In a further embodiment, activated fatty acids may be administered to limit tissue inflammatory injury and inhibit the proliferation of vascular smooth muscle cells by increasing cellular levels of nuclear factor erythroid 2-related factor-2 (Nrf-2) which may be useful in the treatment of a number of vascular diseases. In some embodiments, activated fatty acids may be administered to modify the activity of transient receptor potential (TRP) channels such as TRPA1 and TRPV1 and may be capable of modifying pain and inflammatory signaling. In other embodiments, activated fatty acids may be used to induce heat shock factor (HSF) proteins and inhibit protein tyrosine phosphatases (PTPs), and in still other embodiments, activated fatty acids may be administered to activate mitogen-activated protein kinases (MAP kinases).

In a still further embodiment, activated fatty acids may be useful for ischemic preconditioning. For example, nitrated fatty acids produced by mitochondria in cells under ischemic conditions cause a number of physiological changes within the cell that increases cell survival under ischemic conditions. By providing activated fatty acids to an individual, similar ischemic preconditioning may be achieved allowing for improved survival of, for example, cardiac tissue under ischemic conditions or organs being preserved for optimizing viability and function upon transplantation.

The activated fatty acids of the invention can be administered in any conventional manner by any route where they are active. Administration can be systemic or local. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. In certain embodiments, the administration may be parenteral or intravenous, all in the presence or absence of stabilizing additives that favor extended systemic uptake, tissue half-life and intracellular delivery. Thus, modes of administration for the compounds of the present invention (either alone or in combination with other pharmaceuticals) can be injectable (including short-acting, depot, implant and pellet forms injected subcutaneously or intramuscularly). In some embodiments, an injectable formulation including an activated fatty acid may be deposited to a site of injury or inflammation, such as, for example, the site of a surgical incision or a site of inflammation due to arthroscopy, angioplasty, stent placement, by-pass surgery and so on.

In certain other embodiments, the compounds of the invention may be applied locally as a salve or lotion applied directly to an area of inflammation. For example, in some embodiments, a lotion or salve including activated fatty acids of the invention may be prepared and applied to a burn, radiation burn, site of dermal disorder, edema, arthritic joint or the like.

Various embodiments of the invention are also directed to method for administering activated fatty acids. Specific modes of administration may vary and may depend on the indication. The selection of the specific route of administration and the dose regimen may be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). Those skilled in the art will appreciate that dosages may be determined with guidance, for example, from Goodman & Goldman's The Pharmacological Basis of Therapeutics, Ninth Edition (1996), Appendix II, pp. 1707-1711 or from Goodman & Goldman's The Pharmacological Basis of Therapeutics, Tenth Edition (2001), Appendix II, pp. 475-493 both of which are hereby incorporated by reference in their entireties. With respect to conventional prenylation enzyme inhibitors, guidance may be obtained from art-recognized dosage amounts as described, for example, by J. E. Karp, et al., Blood, 97(11):3361-3369 (2001) and A. A. Adjei, et al., Cancer Research, 60:1871-1877 (2000) hereby incorporated by reference in its entirety.

In various embodiments, an effective amount of an activated fatty acid delivered during each administration cycle may range from about 10 mg/m$^2$/day to about 1000 mg/m$^2$/day. In some embodiments, an effective amount may be about 20 mg/m$^2$/day to about 700 mg/m$^2$/day, and in others, an effective amount may be about 30 mg/m$^2$/day to about 600 mg/m$^2$/day. In particular embodiments, an effective amount may be about 50 mg/m$^2$/day, about 400 mg/m$^2$/day, about 500 mg/m$^2$/day, or about 600 mg/m$^2$/day. In yet other embodiments, an effective amount of an activated fatty acid may vary as treatment progresses. For example, a dosage regimen may be increased or decreased as treatment proceeds through administration cycles, or the daily dosage may increase or decrease throughout administration. In additional embodiments, greater than 1000 mg/m$^2$/day may be administered because even high doses of activated fatty acid are generally tolerable to the patient and may not produce undesired physiological effects.

In some embodiments, the dosage regimen as described above may be combined with a secondary form of treatment or a secondary agent The activated fatty acids of various embodiments may be prepared by any method known in the art. For example, in one embodiment, an activated fatty acid may be prepared by:
i) contacting an unsaturated fatty acid with a mercuric salt and a selenium compound;
ii) contacting the intermediate resulting from step a) with a reagent or reactant that can introduce an electron withdrawing group; and
iii) reacting the intermediate resulting from step b) with an oxidizing agent.

Without wishing to be bound by theory, a selenium compound, such as, for example, PhSeBr, PhSeCl, PhSeO$_2$CCF$_3$, PhSeO$_2$H, PhSeCN and the like, may react with one or more carbon-carbon double bond of the unsaturated fatty acid to form a three-membered ring intermediate on the fatty acid in a reaction that may be facilitated by the mercuric salt such as, for example, HgCl$_2$, Hg(NO$_3$)$_2$, Hg(OAc)$_2$ and the like as depicted in step I of the reaction below:

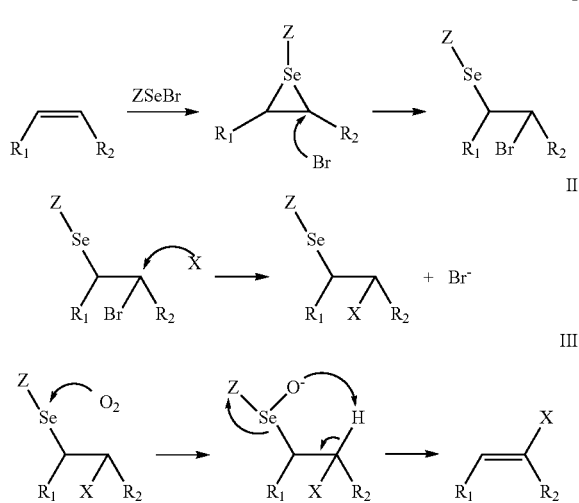

The source of the electron withdrawing group may be any compound known in the art that is capable of generating an electron withdrawing group that can be incorporated into the activated fatty acid, such as, for example, NaNO$_2$, AgNO$_2$, HSO$_2$OH, and the like. Without wishing to be bound by theory, the electron withdrawing group (X in the reaction scheme above) may become joined to the hydrocarbon chain by displacing, for example, the bromine that was associated with the selenium compound as depicted in step II of the reaction scheme provided above. It is noted that the electron withdrawing groups may also react directly with the three-membered ring episelenonium ion shown in step I at the position where the bromine is shown as attacking. Finally, as depicted in step III of the reaction scheme provided above, the oxidizing agent forms a reactive selenium-oxo functional group, which undergo molecular rearrangement and elimination of ZSeOH leading to formation of the electron withdrawing vinyl (depicted as a nitro vinyl) on the hydrocarbon chain. Z in the reaction scheme above may be any number of groups. For example, in certain embodiments, Z may be a phenyl group.

In other embodiments, an activated fatty acid may be prepared using a modified aldol condensation such as the Henry reaction. A review of the Henry reaction and methods related to the Henry method can be found, for example, in Frederick A. Luzzio, F. A. "The Henry reaction: recent examples" Tetrahedron 2001, 57, 915-945 which is hereby incorporated by reference in its entirety. Known variations of the Henry reaction may also be useful in preparing activated fatty acids and all such methods are embodied herein. For example, in some embodiments, variations of the Henry reaction including, but not limited to, the Wittig-like variation of the Henry reaction, the Horner-Wadsworth-Emmons variation of the Henry reaction, and the Peterson-olefination variation of the Henry reaction. In such methods, double bonds are formed using the assistance of groups temporarily included in the reactants but that do are not included in the product. For example, the Wittig reaction uses phosphorus ylides to aid in the condensation reactions with carbonyls and in the dehydration reaction to form alkenes. The Horner-Wadsworth-Emmons reaction uses phosphonate esters, and the Peterson olefination uses silicon reagents for the condensation and dehydration steps. A review of major alkene-forming name reactions by reaction of a functionalized reagent with a carbonyl compound including the Wittig reaction, Horner-Wittig, Horner-Wadsworth-Emmons can be found, for example, in Peterson, Johnson, and Julia reactions. Blakemore, P. R. "The modified Julia olefination: alkene synthesis via the condensation of metallated heteroarylalkylsulfones with carbonyl compounds J. Chem. Soc., Perkin Trans. 1, 2002, 2563-2585 which is hereby incorporated by reference in its entirety.

The Henry "nitro-aldol" reaction is the condensation of a nitroalkane with either an aldehyde or a ketone carbonyl containing compound to form a nitro-aldo product with the newly-formed beta-hydroxynitroalkyl group. Dehydration (loss of water) from nitro-aldol products leads to the formation of nitroalkenes. There are many methods to perform the nitroalkane-carbonyl condensation reaction to make nitro-aldols and there are many methods for the dehydration reaction to form nitroalkenes. Examples of such methods can be found in, for example, Woodcock, S. R.; Marwitz, A. J. V. Bruno, P.; Branchaud, B. P. "Synthesis of Nitrolipids. All Four Possible Diastereomers of Nitrooleic Acids: (E)- and (Z)-, 9- and 10-Nitro-octadec-9-enoic Acids" Organic Letters, 2006, 8, 3931-3934 which provides one regioisomer and usually one of two possible alkene cis/trans or Z/E diastereomers, in high purity and usually in high chemical yield, which is hereby incorporated by reference in its entireties.

Enantioselective Henry reactions are also possible and may require the use of one or more catalysts for the reaction, and embodiments of the invention, include the use of such methods to prepare stereospecific isomers of nitroalkenes. For example, Boruwa, J.; Gogoi, N.; Saikia, P. P.; and Barua, N.C. "Catalytic Asymmetric Henry Reaction" Tetrahedron: Asymmetry 2006, 17, 3315-3326 which is hereby incorporated by reference in its entirety, describes methods for preparing stereospecific isomers of nitoralkenes.

In still other embodiments, alkenes (olefins) may be prepared by metal-mediated cross coupling reactions (joining together of two molecules to make one new molecule) by condensation onto a carbonyl compound. Such methods have not been applied to the formation of nitroalkenes or to the formation of other alkenes with electron-withdrawing substituents, but such methods could be adapted to the synthesis of alkenes with electron-withdrawing substituents. For example, named cross coupling reactions such as the Heck, Suzuki and Stille coupling, along with others may be used to prepare activated fatty acids. Such methods are well known in the art. A review of such reactions of can be found in, for example, Metal-Catalyzed Cross-Coupling Reactions de Meijere, Armin/Diederich, François (eds.) Wiley-VCH, Weinheim 2004. XXII, ISBN-10: 3-527-30518-1 and ISBN-13: 978-3-527-30518-6 which are hereby incorporated by reference in their entireties.

Examples of various embodiments of methods for preparing activated fatty acids may at least include the following steps:
i) combining a first component at least including an aliphatic hydrocarbon having an electron withdrawing group at one end with an second component including aliphatic hydrocarbon chain having an aldehyde at one end in the presence of a base to form a first intermediate; and
ii) generating an alkene from the first intermediate.

Exemplary reactions are presented in schemes I and II below:

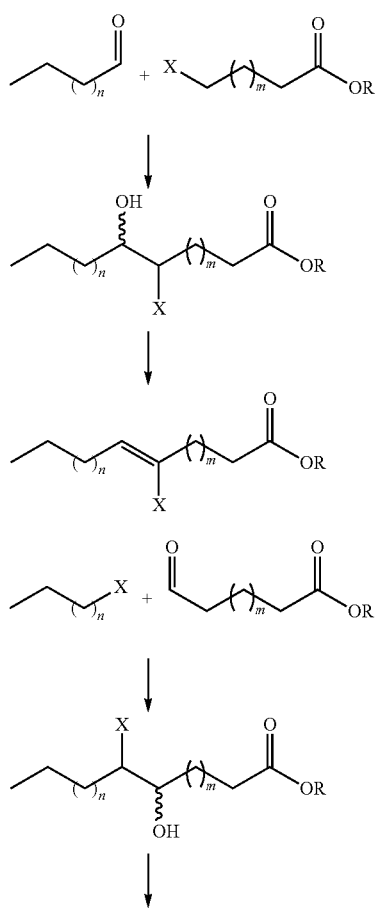

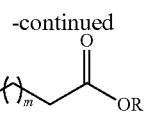

In reaction schemes I and II, the variable X represents an electron withdrawing group and can be any electron withdrawing group discussed herein above or known in the art. The variables n and m represent a number of carbon atoms in the aliphatic hydrocarbon chain, and n and m can be any number. For example, the aliphatic hydrocarbon chains of any of the starting compound may be from 2-20 carbons in length. Moreover, the position of the double bond and the arrangement of the electron withdrawing group in relation to the double bond may be determined specifically, and particular activated fatty acids may be created in high yield. For example, an oleic acid may be produced by the reaction of scheme I by combining a first substrate where m is 10 and a second substrate where n is 2.

Any activated fatty acid may be produced using the method presented above, and both naturally-occurring and naturally or non-naturally-occurring analogs may be synthesized.

For example, synthesis of an exemplary nitrated fatty acids may be produced as illustrated in the general synthetic method is shown in III, below.

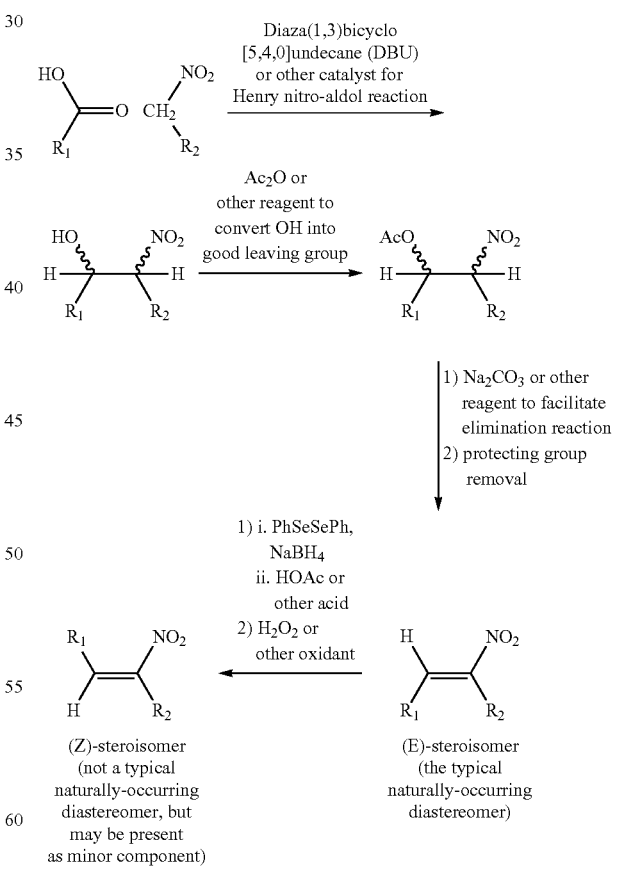

In such embodiments, $R_1$ and $R_2$ can include any number of carbons. For example in one embodiment, a naturally occurring fatty acid having an even number of carbons (20 carbons total, in this case) may be prepared from components where $R_2$ is $CH_2CH_3$ and $R_1$ is $(CH_2)_{15}CO_2R_3$, where $R_3$ is a protecting group for the carboxylic acid functional group found in fatty acids. Similarly, a naturally or non-naturally occurring fatty acid having an odd number of carbons (19 carbons total, in this case) may be prepared from components where $R_2$ is $CH_2CH_3$ and $R_1$ is $(CH_2)_{14}CO_2R_3$, where $R_3$ is a protecting group for the carboxylic acid functional group found in fatty acids. The method illustrated in scheme III can be applied to the synthesis of essentially any nitrated lipid having either an even or an odd number of carbons by incorporating different $R_1$ and $R_2$ groups. For example, each of $R_1$ and $R_2$ may be an aliphatic or substituted aliphatic carbon chain having from 1 to 20 carbons, although any greater number of carbons is also possible. Moreover, individual $R_1$ and/or $R_2$ groups may include any number of carbon-carbon double bonds, which may or may not include associated electron withdrawing groups attached to an alpha, beta, or gamma carbon of the carbon-carbon double bond. Similarly, individual $R_1$ and $R_2$ groups may include branched chains. In such embodiments, the additional carbon-carbon double bonds associated with $R_1$ and/or $R_2$ may be conjugated, unconjugated, or partially conjugated with one another or will become conjugated with a carbon-carbon double bond created as a result of the reaction. As indicated above, the reaction depicted in scheme III may be carried out sequentially to create an activated fatty acid having more than one carbon-carbon double bond with associated electron withdrawing groups. In such embodiments, individual $R_1$ and $R_2$ groups for each reaction in a sequence may be from 1 to about 12 carbons, although any greater number of carbons is also possible.

In some embodiments, individual $R_1$ and $R_2$ groups may contain additional functional groups other than double bonds, which may or may not be associated with a carbon-carbon double bond either existing before the reaction is carried out or following the reaction illustrated in Scheme III. For example, individual $R_1$ and $R_2$ groups may include functional groups such as, but not limited to, alkynes, as a part of the chain, with the alkyne in the chain, alcohols, aldehyde carbonyls, ketone carbonyls, derivatives of carbonyl aldehydes and ketones, such as, oximes, hydrazones and any other carbonyl derivative known in the art, amines, amines with other groups known in the art attached to the amine, thiols, thiols with other groups known in the art attached to the thiols, any other functional group known in the art, either as the simple functional group or the functional group with another chain or group attached to it. Such functional groups may be attached to a carbon in the linear or branched chain. Without wishing to be bound by theory, the addition of additional functional groups may alter the targeting and bioavailability of the activated fatty acids of embodiments, such that specific cells or targets it within cells can be targeted.

In yet other embodiments, molecules may contain more than one carbon chain, with two or more carbon chains joined together by a non-carbon group, and in some embodiments, each of the carbon chains can be branched or linear. For example, in certain embodiments, non-carbon functional groups that can join two or more carbon chains together include, but are not limited to, those in the very common functional groups listed below:

Ethers $R_1$—O—$R_2$,
Amines $R_1$—$NR_3$—$R_2$,
Esters $R_1$—C(=O)—O—$R_2$,
Amides $R_1$—C(=O)—$NR_3$—$R_2$
ThioEsters $R_1$—C(=S)—O—$R_2$ or $R_1$—C(=O)—S—$R_2$
ThioAmides $R_1$—C(=S)—$NR_3$—$R_2$ In addition to the common non-carbon multivalent elements found in organics compounds and shown above (oxygen, nitrogen & sulfur), other functional groups known in the art, and based on any other non-carbon multivalent element may be used in embodiments of the invention. In various embodiments, any of the non-carbon chains described above could be incorporated into activated fatty acids using the general synthetic approach shown in III, above, in which the non-carbon chains are in $R_1$, $R_2$ or both.

Preparation of heteroatom containing activated fatty acids may be carried out using the same methodology as described above for introducing an electron withdrawing group to an unsaturated fatty acid. For example, in some embodiments, an unsaturated aliphatic chain containing toluenesulfonate may be combined with a mercaptoalkanoic acid such as, for example, an 2-mercaptoacetic acid or 3-mercaptopropionic acid, or an hydroxyalkanoic acid such as, for example, 2-hydroxyacetic acid or 3-hydroxypropionic acid, in an appropriate solvent to produce a thioalkanoic acid or oxyalkanoic acid covalently attached to the unsaturated or polyunsaturated aliphatic chain, and in other embodiments, an unsaturated aliphatic chain containing a halogen such as, for example, a Cl or Br, end group be combined with a mercaptoalkanoic acid such as, for example, 2-mercaptoacetic acid or 3-mercaptopropionic acid, or an hydroxyalkanoic acid such as, for example, 2-hydroxyacetic acid or 3-hydroxypropionic acid, in an appropriate solvent to produce a thioalkanoic acid or oxyalkanoic acid, covalently attached to the unsaturated or polyunsaturated aliphatic chain. In still other embodiments, a sulfinylalkanoic acid may be prepared by drying a thioalkanoic acid prepared as described above and maintaining the dried product in an oxygen rich environment for a several days. In such embodiments, an electron withdrawing group may be introduced onto the unsaturated or polyunsaturated aliphatic chain by any of the methods provided above either before or after formation of the thioalkanoic acid, oxyalkanoic acid, or sulfinylalkanoic acid.

Pharmaceutical formulations containing the compounds of the invention and a suitable carrier can be in various forms including, but not limited to, solids, solutions, powders, fluid emulsions, fluid suspensions, semi-solids, and dry powders including an effective amount of an activated fatty acid of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, antioxidants, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's*, The Pharmaceutical Basis of Therapeutics, 6th Edition, MacMillan Publishing Co., New York (1980) both of which are hereby incorporated by reference in their entireties can be consulted.

The compounds of the present invention can be formulated for parenteral or intravenous administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids diluents such as oleic acid find use in the preparation of injectables. Additional fatty acids diluents that may be useful in embodiments of the invention include, for example, one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, and the like. In some embodiments, the fatty acid diluent may be a mixture of fatty acids. In some embodiments, the fatty acid may be a fatty acid ester, a sugar ester of fatty acid, a glyceride of fatty acid, or an ethoxylated fatty acid ester, and in other embodiments, the fatty acid diluent may be a fatty alcohol such as, for example, stearyl alcohol, lauryl alcohol, palmityl alcohol, palmitolyl acid, cetyl alcohol, capryl alcohol, caprylyl alcohol, oleyl alcohol, linolenyl alcohol, arachidonic alcohol, behenyl alcohol, isobehenyl alcohol, selachyl alcohol, chimyl alcohol, and linoleyl alcohol and the like and mixtures thereof.

Other embodiments of the invention include activated fatty acid prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

Preparation of an activated fatty acid in solid dosage form may vary. For example, in one embodiment, a liquid or gelatin formulation of the activated fatty acid may be prepared by combining the activated fatty acid with one or more fatty acid diluent, such as those described above, and adding a thickening agent to the liquid mixture to form a gelatin. The gelatin may then be encapsulated in unit dosage form to form a capsule. In another exemplary embodiment, an oily preparation of an activated fatty acid prepared as described above may be lyophilized to for a solid that may be mixed with one or more pharmaceutically acceptable excipient, carrier or diluent to form a tablet, and in yet another embodiment, the activated fatty acid of an oily preparation may be crystallized to from a solid which may be combined with a pharmaceutically acceptable excipient, carrier or diluent to form a tablet.

Further embodiments which may be useful for oral administration of activated fatty acids include liquid dosage forms. In such embodiments, a liquid dosage may include a pharmaceutically acceptable emulsion, solution, suspension, syrup, and elixir containing inert diluents commonly used in the art, such as water. Such compositions may also comprise adjuvants, such as wetting agents, emulsifying and suspending agents, and sweetening, flavoring, and perfuming agents.

In still further embodiments, activated fatty acids of the invention can be formulated as a depot preparation. Such long acting formulations can be administered by implantation (for example, subcutaneously or intramuscularly) or by intramuscular injection. Depot injections can be administered at about 1 to about 6 months or longer intervals. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Other suitable diluents for injectable formulations include, but are not limited to those described below:

Vegetable oil: As used herein, the term "vegetable oil" refers to a compound, or mixture of compounds, formed from ethoxylation of vegetable oil, wherein at least one chain of polyethylene glycol is covalently bound to the vegetable oil. In some embodiments, the fatty acids has between about twelve carbons to about eighteen carbons. In some embodiments, the amount of ethoxylation can vary from about 2 to about 200, about 5 to 100, about 10 to about 80, about 20 to about 60, or about 12 to about 18 of ethylene glycol repeat units. The vegetable oil may be hydrogenated or unhydrogenated. Suitable vegetable oils include, but are not limited to castor oil, hydrogenated castor oil, sesame oil, corn oil, peanut oil, olive oil, sunflower oil, safflower oil, soybean oil, benzyl benzoate, sesame oil, cottonseed oil, and palm oil. Other suitable vegetable oils include commercially available synthetic oils such as, but not limited to, Miglyol™ 810 and 812 (available from Dynamit Nobel Chemicals, Sweden) Neobee™ M5 (available from Drew Chemical Corp.), Alofine™ (available from Jarchem Industries), the Lubritab™ series (available from JRS Pharma), the Sterotex™ (available from Abitec Corp.), Softisan™ 154 (available from Sasol), Croduret™ (available from Croda), Fancol™ (available from the Fanning Corp.), Cutina™ HR (available from Cognis), Simulsol™ (available from CJ Petrow), EmCon™ CO (available from Amisol Co.), Lipvol™ CO, SES, and HS-K (available from Lipo), and Sterotex™ HM (available from Abitec Corp.). Other suitable vegetable oils, including sesame, castor, corn, and cottonseed oils, include those listed in R. C. Rowe and P. J. Shesky, *Handbook of Pharmaceutical Excipients*, (2006), 5th ed., which is incorporated herein by reference in its entirety. Suitable polyethoxylated vegetable oils, include but are not limited to, Cremaphor™ EL or RH series (available from BASF), Emulphor™ EL-719 (available from Stepan products), and Emulphor™ EL-620P (available from GAF).

Mineral oils: As used herein, the term "mineral oil" refers to both unrefined and refined (light) mineral oil. Suitable mineral oils include, but are not limited to, the Avatech™ grades (available from Avatar Corp.), Drakeol™ grades (available from Penreco), Sirius™ grades (available from Shell), and the Citation™ grades (available from Avater Corp.).

Castor oils: As used herein, the term "castor oil", refers to a compound formed from the ethoxylation of castor oil, wherein at least one chain of polyethylene glycol is covalently bound to the castor oil. The castor oil may be hydrogenated or unhydrogenated. Synonyms for polyethoxylated castor oil include, but are not limited to polyoxyl castor oil, hydrogenated polyoxyl castor oil, mcrogolglyceroli ricinoleas, macrogolglyceroli hydroxystearas, polyoxyl 35 castor oil, and polyoxyl 40 hydrogenated castor oil. Suitable polyethoxylated castor oils include, but are not limited to, the Nikkol™ HCO series (available from Nikko Chemicals Co. Ltd.), such as Nikkol HCO-30, HC-40, HC-50, and HC-60 (polyethylene glycol-30 hydrogenated castor oil, polyethylene glycol-40 hydrogenated castor oil, polyethylene glycol-50 hydrogenated castor oil, and polyethylene glycol-60 hydrogenated castor oil, Emulphor™ EL-719 (castor oil 40 mole-ethoxylate, available from Stepan Products), the Cremophore™ series (available from BASF), which includes Cremophore RH40, RH60, and EL35 (polyethylene glycol-40 hydrogenated castor oil, polyethylene glycol-60 hydrogenated castor oil, and polyethylene glycol-35 hydrogenated castor oil, respectively), and the Emulgin® RO and HRE series (available from Cognis PharmaLine). Other suitable polyoxyethylene castor oil derivatives include those listed in R. C. Rowe and P. J. Shesky, *Handbook of Pharmaceutical Excipients*, (2006), 5th ed., which is incorporated herein by reference in its entirety.

Sterol: As used herein, the term "sterol" refers to a compound, or mixture of compounds, derived from the ethoxylation of sterol molecule. Suitable polyethoyxlated sterols include, but are not limited to, PEG-24 cholesterol ether, Solulan™ C-24 (available from Amerchol); PEG-30 cholestanol, Nikkol™ DHC (available from Nikko); Phytosterol, GENEROL™ series (available from Henkel); PEG-25 phyto sterol, Nikkol™ BPSH-25 (available from Nikko); PEG-5 soya sterol, Nikkol™ BPS-5 (available from Nikko); PEG-10 soya sterol, Nikkol™ BPS-10 (available from Nikko); PEG-20 soya sterol, Nikkol™ BPS-20 (available from Nikko); and PEG-30 soya sterol, Nikkol™ BPS-30 (available from Nikko). As used herein, the term "PEG" refers to polyethylene glycol.

Polyethylene glycol: As used herein, the term "polyethylene glycol" or "PEG" refers to a polymer containing ethylene glycol monomer units of formula —O—$CH_2$—$CH_2$—. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer. In some embodiments, the polyethylene glycol is polyethylene glycol-400. Suitable polyethylene glycols include, but are not limited to the Carbowax™ and Carbowax™ Sentry series (available from Dow), the Lipoxol™ series (available from Brenntag), the Lutrol™ series (available from BASF), and the Pluriol™ series (available from BASF).

Propylene glycol fatty acid ester: As used herein, the term "propylene glycol fatty acid ester" refers to an monoether or diester, or mixtures thereof, formed between propylene glycol or polypropylene glycol and a fatty acid. Fatty acids that are useful for deriving propylene glycol fatty alcohol ethers include, but are not limited to, those defined herein. In some embodiments, the monoester or diester is derived from propylene glycol. In some embodiments, the monoester or diester has about 1 to about 200 oxypropylene units. In some embodiments, the polypropylene glycol portion of the molecule has about 2 to about 100 oxypropylene units. In some embodiments, the monoester or diester has about 4 to about 50 oxypropylene units. In some embodiments, the monoester or diester has about 4 to about 30 oxypropylene units. Suitable propylene glycol fatty acid esters include, but are not limited to, propylene glycol laurates: Lauroglycol™ FCC and 90 (available from Gattefosse); propylene glycol caprylates: Capryol™ PGMC and 90 (available from Gatefosse); and propylene glycol dicaprylocaprates: Labrafac™ PG (available from Gatefosse).

Stearoyl macrogol glyceride: Stearoyl macrogol glyceride refers to a polyglycolized glyceride synthesized predominately from stearic acid or from compounds derived predominately from stearic acid, although other fatty acids or compounds derived from other fatty acids may used in the synthesis as well. Suitable stearoyl macrogol glycerides include, but are not limited to, Gelucire® 50/13 (available from Gattefossé).

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

Exemplary excipients or carriers for use in solid and/or liquid dosage forms include, but are not limited to:

Sorbitol: Suitable sorbitols include, but are not limited to, PharmSorbidex E420 (available from Cargill), Liponic 70-NC and 76-NC (available from Lipo Chemical), Neosorb (available from Roquette), Partech SI (available from Merck), and Sorbogem (available from SPI Polyols).

Starch, sodium starch glycolate, and pregelatinized starch include, but are not limited to, those described in R. C. Rowe and P. J. Shesky, *Handbook of Pharmaceutical Excipients*, (2006), 5th ed., which is incorporated herein by reference in its entirety.

Disintegrant: The disintegrant may include one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

Still further embodiments of the invention include activated fatty acids administered in combination with other active such as, for example, adjuvants, protease inhibitors, or other compatible drugs or compounds where such combination is seen to be desirable or advantageous in achieving the desired effects of the methods described herein.

This invention and embodiments illustrating the method and materials used may be further understood by reference to the following non-limiting examples.

EXAMPLE 1

Preparation of (E)-9-nitro-octadec-9-enoic acid

Commercially available 9-bromononanol was oxidized using Jones' reagent, chromium trioxide ($CrO_3$) in concentrated sulfuric acid ($H_2SO_4$), 67%, to form a carboxylic acid protected as an allyl ester (92% yield) and was nitrated using the Kornblum method, silver nitrate ($AgNO_2$) in diethyl ether ($Et_2O$), to form 9-nitro-nonanoic acid, allyl ester, in an overall yield of 42%. Nitroaldol condensation was then carried out by combining this intermediate with commercially available nonyl aldehyde in the presence of a catalytic amount of (10 mol %) of DBU to produce β-hydroxynitro (81% yield) as a 1:1 mixture of diastereomers. The β-hydroxynitro ester intermediate was acetylated in acetic anhydride with a catalytic amount of p-toluenesulfonic acid to produce a β-acetoxynitro ester intermediate in high yield, and the nitroalkene was generated by from the β-acetoxynitro ester intermediate by base-induced elimination with azeotropic removal of water in 0.5 equivalence of sodium carbonate. The stereoselectively clean (E)-isomer nitroalkene was produced in 84% yield and did not require isomerization or deconjugation of double bonds to form allylic nitroalkanes. A free acid of the produced nitroalkene was accomplished by palladium catalyzed isomerization in the presence of formic acid to produce the free acid (E)-9-nitro-octadec-9-enoic acid in 95% yield. Overall yield from commercially available starting products was 56%. Because of the base sensitivity of nitroalkenes acidic conditions were consistently throughout both reaction and work-up were possible.

EXAMPLE 2

Preparation of (E)-3-(8-nitroheptadec-8-enylthio)acetic acid

2-Mercaptoacetic acid (288 mg, 3.13 mmol) can be added under nitrogen to a stirred solution of sodium methoxide, prepared from 180 mg (7.83 mmol) of sodium and 20 mls of methanol. After dissolution, a solution of (E)-1-bromo-9-nitro-octadec-9-ene (725 mg, 2.61 mmol) in diethyl ether (2 ml) can be added and mixture can be stirred for about 16 hours at room temperature. The crude reaction mixture can be poured into an equal volume of hydrochloric acid, the organic phase can be separated and washed with water, and the solution can be dried over sodium sulfate.

(E)-1-bromo-9-nitro-octadec-9-ene can be prepared by bromination of (E)-9-nitro-octadec-9-enoic acid.

EXAMPLE 3

Preparation of Nitrated Linoleic Acid

Any nitrated linoleic acid or oleic acid described in U.S. patent application Ser. No. 11/568,377, which is hereby incorporated by reference in its entirety, can be nitrated by bromination of a nitrated linoleic acid or oleic acid by conventional means and adding the brominated nitrated linoleic acid in diethyl ether to 2-Mercaptoacetic acid (288 mg, 3.13 mmol) that has been stirred under nitrogen in a solution of sodium methoxide, prepared from 180 mg (7.83 mmol) of sodium and 20 mls of methanol. The resulting mixture can be stirred for about 16 hrs at room temperature. The crude reaction mixture can be poured into an equal volume of hydrochloric acid, the organic phase can be separated and washed with water, and the solution can be dried over sodium sulfate.

EXAMPLE 4

Preparation of 3-(3E,6E)-6-nitronona-3,6-dienylthiopropionic acid

3-Mercaptopropionic acid (150 mg, 1.41 mmol, 1.5 eq) can be added, under an atmosphere of dry nitrogen, to a stirred solution of sodium methoxide, prepared from sodium (64 mg, 2.78 mmol, 3 eq) and methanol (20 ml). After the initial white precipitate had dissolved, a solution of (3Z,6Z)-nona-3,6-dienyl p-toluenesulfonate (276 mg, 0.94 mmol) in diethyl ether can be added. The mixture can be stirred at 40° C. for several days under nitrogen, hydrochloric acid (10% v/v, 20 ml) and diethyl ether (20 ml) can be poured into the crude reaction mixture. The organic phase can be collected and washed with water and brine, and dried over sodium sulfate. The 3-(3E,6E)-nona-3,6-dienylthiopropionic acid produced can be dissolved in a solvent and PhSeBr and $HgCl_2$ can added to the solution followed by an oxidizing agent to form a nitro-vinyl group at either on the 3-(3E,6E)-nona-3,6-dienylthiopropionic acid thereby producing, 3-(3E,6E)-6-nitronona-3,6-dienylthiopropionic acid.

(3Z,6Z)-nona-3,6-dienyl p-toluenesulfonate can be prepared from 2-Pentyn-1-ol by dissolving 2-Pentyn-1-ol (1.03 g, 12 mmol) in chloroform (10 ml) and adding pyridine (1.90 g, 24 mmol) followed by p-toluenesulfonyl chloride (3.43 g, 18 mmol) in small portions with constant stirring. After about 4 hrs, ether (30 ml) and water (7 ml) can be added and the organic layer can be washed successively with HCl (7 ml), 5% $NaHCO_3$, water (7 ml) to produce pent-2-ynyl p-toluenesolfonate. Pent-2-ynyl p-toluenesolfonate (1.37 g, 5.78 mmol, 1.1 eq) can be added at low temperature under nitrogen to a well-stirred suspension in DMF (15 ml) of but-3-yn-1-ol (368 mg, 5.25 mmol), sodium carbonate (834 mg, 7.87 mmol), tetrabutylammonium chloride (1.46 g, 5.25 mmol) and copper(I) iodide (1.00 g, 5.25 mmol). The mixture can then be stirred at room temperature for about 48 hrs, and ether (30 ml) and 1M HCl (30 ml) can be added, the organic phase can be collected and washed with brine, and dried over sodium sulfate to produce nona-3,6-diyn-1-ol. Nona-3,6-diyn-1-ol (198 mg, 1.45 mmol) can be hydrogenated at atmospheric pressure, in the presence of a mixture of quinoline (44 mg) and palladium (5%) on calcium carbonate (100 mg), poisoned with lead in methanol (25 ml). After several hours, the methanol can be evaporated in vacuo, quinoline can be removed by silica gel column chromatography using ether-hexane (35:65) as the eluent to produce (3Z,6Z)-nona-3,6-dien-1-ol. (3Z,6Z)-Nona-3,6-dien-1-ol (167 mg, 1.19 mmol) can be dissolved in chloroform (5 ml) and the solution can be cooled in an ice bath. Pyridine (376 mg, 4.76 mmol) can be added, followed by p-toluenesulfonyl chloride (340 mg, 1.78 mmol) in small portions with constant stirring. The mixture can be stirred for about 24 hrs at low temperature, and ether (15 ml) and water (5 ml) can be added, the organic layer can be collected and washed successively with 1 N HCl (10 ml), 5% $NaHCO_3$, water (10 ml), and brine (10 ml), and then dried over $Na_2SO_4$ to produce (3Z,6Z)-nona-3,6-dienyl p-toluenesulfonate.

EXAMPLE 5

Production of (Z)-isomers (Z)-9-nitro-octadec-9-enoic was formed from the (E)-9-nitro-octadec-9-enoic acid using the Ono method as described in Ono, N, et al. J. Chem. Soc., Chem. Commun. 1987, 1551-1551 and Sharpless et al., Am. Chem. Soc. 1973, 95, 2697-2699, both of which are hereby incorporated by reference in their entireties, at about 80% to about 90% yield.

What is claimed is:

1. An activated fatty acid comprising a hydrochloride salt of an unsaturated or polyunsaturated aliphatic chain having at least one electron withdrawing group positioned immediately adjacent to a carbon-carbon double bond wherein two or more carbon-carbon double bonds are conjugated; wherein the at least one electron withdrawing group is selected from the group consisting of a vinyl group, an allylic group, or an allyl fluoride ($-CH=CHCH_2F$) group.

2. The activated fatty acid of claim 1, wherein the unsaturated or polyunsaturated aliphatic chain comprises from about 4 to about 25 carbons.

3. The activated fatty acid of claim 1, wherein the unsaturated or polyunsaturated aliphatic chain is selected from the group consisting of glycolipids, glycerolipids, phospholipids, and a cholesterol esters.

4. The activated fatty acid of claim 1, further comprising an additional electron withdrawing group selected from the group consisting of aldehyde (COH), acyl ($-COR$), carbonyl ($-CO$), carboxylic acid ($-COOH$), ester ($-COOR$), halides ($-Cl$, $-F$, $-Br$, $-I$), fluoromethyl ($-CF_n$), allyl fluoride ($-CH=CHCH_2F$), cyano ($-CN$), sulfoxide ($-SOR$), sulfonyl ($-SO_2R$), sulfonic acid ($-SO_3H$), 1°, 2°, and 3° ammonium ($-NR_3^+$), or nitro ($-NO_2$), wherein R is selected from the group consisting of hydrogen, methyl, and $C_2$-$C_6$ alkyl.

5. The activated fatty acid of claim 1, further comprising an additional electron withdrawing group wherein the additional electron withdrawing group is a nitro ($-NO_2$) group.

6. The activated fatty acid of claim 1, wherein the at least one electron withdrawing group is positioned on an alpha carbon of a carbon-carbon double bond of the unsaturated or polyunsaturated aliphatic chain.

7. The activated fatty acid of claim 1, wherein the at least one electron withdrawing group is positioned on a beta carbon of a carbon-carbon double bond of the unsaturated or polyunsaturated aliphatic chain.

8. The activated fatty acid of claim 1, wherein the at least one electron withdrawing group is positioned on a gamma carbon of a carbon-carbon double bond of the unsaturated or polyunsaturated aliphatic chain.

9. The activated fatty acid of claim 1, wherein a carbon-carbon double bond associated with the at least one electron withdrawing group is in a configuration selected from the group consisting of cis and trans.

10. The activated fatty acid of claim 1, wherein the unsaturated or polyunsaturated aliphatic chain comprises 18 carbons and the at least one electron withdrawing group is at a position selected from the group consisting of C-9, C-10, C-12, C-13, and a combination thereof.

11. The activated fatty acid of claim 1, further comprising one or more functional group other than an electron withdrawing group.

* * * * *